(12) United States Patent
Yin et al.

(10) Patent No.: US 9,760,989 B2
(45) Date of Patent: Sep. 12, 2017

(54) VISUALIZATION AND QUANTIFICATION OF LUNG DISEASE UTILIZING IMAGE REGISTRATION

(71) Applicant: Vida Diagnostics, Inc., Coralville, IA (US)

(72) Inventors: Youbing Yin, Coralville, IA (US); Philippe Raffy, Edina, MN (US); Susan A. Wood, Palo Alto, CA (US)

(73) Assignee: VIDA Diagnostics, Inc., Coralville, IA (US)

( * ) Notice: Subject to any disclaimer, the term of this patent is extended or adjusted under 35 U.S.C. 154(b) by 80 days.

(21) Appl. No.: 14/279,207

(22) Filed: May 15, 2014

(65) Prior Publication Data
US 2015/0332454 A1    Nov. 19, 2015

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/50* (2013.01); *A61B 6/5217* (2013.01);
(Continued)

(58) Field of Classification Search
CPC ......... G06T 2207/30061; G06T 7/0012; G06T 15/08; G06T 7/0081; G06T 2207/10072; G06T 2207/10116; G06T 2207/20076; G06T 2207/20081; G06T 7/0024; G06T 7/401; G06K 9/52; G06K 9/6201;
(Continued)

(56) References Cited

U.S. PATENT DOCUMENTS 9,076,201 B1 *  7/2015  Negahdar ............. G06T 7/0012
2005/0190189 A1 *  9/2005  Chefd'hotel .......... G06T 7/0024
                                                                    345/501
(Continued)

FOREIGN PATENT DOCUMENTS

JP         2005028121 A  *  2/2005  ............... A61B 5/08

OTHER PUBLICATIONS

Craig J. Calban, et al., Computed tomography-based biomarker provides unique signature for diagnosis of COPD phenotypes and disease progression., Nov. 2012; pp. 1711 to 1715.
(Continued)

*Primary Examiner* — Tom Y Lu
(74) *Attorney, Agent, or Firm* — Fredrikson & Byron, P.A.

(57) ABSTRACT

Methods and systems for assessing lung function using volumetric images obtained at inspiration and expiration. The method may include processing the first and second set of images to identify known anatomical structures of the lungs, registering the first set of images to the second set of images to match voxels of the first set of images to voxels of the second set of images as matched pairs of inspiratory and expiratory voxels, calculating a continuous probability of a lung characteristic at a location of the matched pairs of voxels, and displaying the result on a display. The method may also include classifying lung tissue at each location as normal, having air trapping without emphysema, or being emphysematous.

20 Claims, 21 Drawing Sheets
(16 of 21 Drawing Sheet(s) Filed in Color)

(51) Int. Cl.
*G06T 15/08* (2011.01)
*G06K 9/62* (2006.01)
*G06K 9/52* (2006.01)
*A61B 6/03* (2006.01)
*A61B 6/00* (2006.01)
*G06T 19/20* (2011.01)
*G06T 7/33* (2017.01)
*A61B 5/091* (2006.01)

(52) U.S. Cl.
CPC .............. *A61B 6/5235* (2013.01); *G06K 9/52* (2013.01); *G06K 9/6201* (2013.01); *G06K 9/6267* (2013.01); *G06T 7/0016* (2013.01); *G06T 7/33* (2017.01); *G06T 15/08* (2013.01); *G06T 19/20* (2013.01); *A61B 5/091* (2013.01); *G06T 2207/10081* (2013.01); *G06T 2207/10088* (2013.01); *G06T 2207/10104* (2013.01); *G06T 2207/30061* (2013.01); *G06T 2219/2012* (2013.01)

(58) Field of Classification Search
CPC ........ G06K 9/6267; A61B 5/08; A61B 6/032; A61B 6/50; A61B 6/5217
See application file for complete search history.

(56) References Cited

U.S. PATENT DOCUMENTS

| | | |
|---|---|---|
| 2011/0243403 A1 | 10/2011 | Mizuno |
| 2012/0249546 A1 | 10/2012 | Tschirren et al. |
| 2014/0105472 A1 | 4/2014 | Yin et al. |

OTHER PUBLICATIONS

International Search Report and Written Opinion for International Application No. PCT/US2015/030704, Aug. 14, 2015, 16 pages.

* cited by examiner

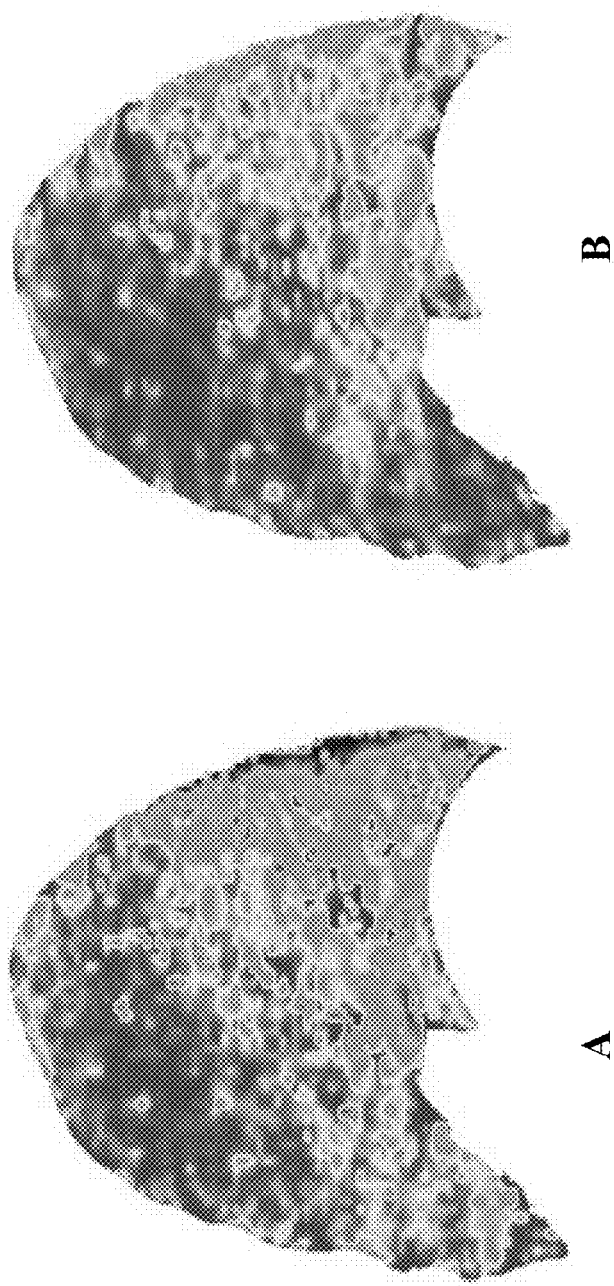
Figure 14
Figure 15

VISUALIZATION AND QUANTIFICATION OF LUNG DISEASE UTILIZING IMAGE REGISTRATION

BACKGROUND OF THE INVENTION

Severe emphysema is a debilitating disease that limits the quality of life of patients and represents an end state of Chronic Obstructive Pulmonary Disease (COPD). It is believed that 3.5 million people in the US have the severe emphysematous form of COPD, and it is increasing in both prevalence and mortality. Current treatment methods for severe emphysema include lung volume reduction (LVR) surgery, which is highly invasive and can be risky and uncomfortable for the patient. New treatment methods for treating emphysema include bronchoscopy guided lung volume reduction devices that aim to close off ventilation to the diseased regions of the lung but maintain ventilation to healthier lung. However, the complex three dimensional structure of the lungs and the diversity of COPD within the lungs of an individual patient makes understanding the disease within each patient difficult.

There are at least two phenotypes of COPD, emphysema and airway obstruction, which is also referred to as air trapping or small airway disease. Emphysema occurs when the lung parenchyma is gradually destroyed, resulting in a loss of elasticity. Small airway disease, in contrast, is characterized by airway inflammation and remodeling, which can lead to airway obstruction and the trapping of gas within the lung. In many patients, COPD progresses from small airway disease to emphysema, which typically includes air trapping as well as a loss of elasticity. In addition, both phenotypes may be present in different portions of a patient's lungs. Understanding and differentiating these two phenotypes is important for understanding the disease process and for selecting treatment for patients.

Currently, airway limitation can be diagnosed by spirometry and is graded into 5 stages according to the Global Initiative for Chronic Obstructive Lung Diseases (GOLD) criteria. In addition, CT images, may be used to characterize the lungs by measuring the Hounsfield Unit (HU) of the CT images at full inspiration and full expiration. Emphysema is diagnosed if the HU is less than −950 in a full inspiration CT scan. Air trapping is diagnosed if the HU is less than −856 HU in an end-expiration or residual volume CT scan. This analysis may be determined using the entire lung, or to a limited extent may be based on different portions of the lung, to identify the presence of emphysema or air trapping in particular portions of the lung. However, because of the dynamic nature of the lung due to the expansion that occurs during breathing, assessment of the presence of COPD by this method using one static image is limited. To overcome this, some measurements have been derived from the pair of inspiration and expiration scans, such as the ratio of mean lung density between expiration and inspiration (E/I ratio) and relative volume changes (RVC) between −850 HU to −950 HU, and they have shown better correlations against clinical metadata. In addition, to further improve upon the methods of CT diagnosis of emphysema and small airway disease in particular locations in the lung, researchers have recently published a method which includes registering (matching) inspiration and expiration CT scans. In particular, like the prior art CT method described above, one method uses defined cut-off values for determining whether emphysema or small airway disease is present at matched locations. An example of such as method has been described by Galban et al., CT-based biomarker provides unique signature for diagnosis of COPD phenotypes and disease progression," Nat. Med., vol. 18, no. 11, pp. 1711-5, November 2012. However, this approach still has limitations.

Another lung disease, lung cancer, is the world's leading cause of cancer death, with more annual deaths (approximately 28% of all cancer deaths) than any other cancers which have routine screening programs such as breast, colorectal and prostate. In 2013, the U.S. mortality rate was 160,340 persons (approximately 28% of all cancer deaths), and an estimated 3,400 lung cancer deaths were among non-smokers caused by exposure to secondhand smoke.

Currently in the U.S., there are 373,489 persons diagnosed with lung cancer with an incidence rate of 226,160 new diagnoses each year (~14% of all cancer diagnoses). However, only 15% of lung cancer cases are diagnosed at an early stage; thus, 85% of diagnosed lung cancer is late stage. For patients diagnosed with lung cancer, there is only 16.3% five-year survival rate. This is much lower than many of the other leading cancers, such as colon (65.2%), breast (90.0%) and prostate (99.9%). The five-year survival rate is much higher in cases where the cancer is detected and localized within the lungs (52.6%), whereas if the cancer has metastasized to other organs, the five-year survival is only 3.5%. Of those diagnosed with lung cancer, over half die within the first year of diagnosis. Early diagnosis is therefore imperative.

CT imaging is also useful for lung cancer screening, and is becoming accepted for patients at high risk of developing lung cancer. These include patients aged 55 to 80 years with a smoking history of 30 pack-year of more who currently smoke or have quit smoking within the past 15 years. However, even among these high risk individuals, some individuals may be more likely to develop lung cancer than others. If additional risk factors could be determined, this would be useful for developing a more refined approach to cancer screening. In this way, the use of expensive CT scans, with the inherent dosing of radiation and the risk of false positive results, could be adjusted according to a more individualized risk analysis.

SUMMARY

Certain embodiments of the present invention are described in the following illustrative embodiments. Various embodiments include methods and systems for assessing lung function and characterizing a patient's lungs using inspiratory and expiratory volumetric images. In some embodiments, the method includes using a first set of lung volumetric images obtained at inspiration and a second set of volumetric images obtained at expiration, processing the first and second set of images to identify known anatomical structures of the lungs, registering the first set of images to the second set of images to match voxels of the first set of images to voxels of the second set of images as matched pairs of inspiratory and expiratory voxels, calculating a continuous probability of a lung characteristic at a location of the matched pairs of voxels, and displaying the result on a display.

In some embodiments, displaying the result includes generating an image depicting a set of data points, wherein each data point represents the calculated continuous probability of the lung characteristic of the matched pairs of voxels. For example, the image may be a 3 dimensional representation of the lungs, wherein each data point is depicted in the representation at a location corresponding to the location of the matched pair of voxels.

In some embodiments, the continuous probability of the lung characteristics is derived from density measurements. The continuous probability of the lung characteristic may be a continuous probability of tissue destruction and a continuous probability of a ventilation deficit.

Displaying the result may include generating a color image depicting a set of data points, wherein the color of each data point represents the calculated continuous probability of the lung characteristic of the matched pairs of voxels, and wherein the color of each data point is a composite of a first color component dependent upon the continuous probability of a ventilation deficit and a second color component dependent upon the continuous probability of tissue destruction. For example, each data point may be displayed on a graph with the probability of tissue destruction on a first scale and probability of ventilation deficit on a second scale. The graph may include a plurality of topographic lines, wherein each topographic line indicates an equal number of data points occurring at all coordinates on each topographic line. In some embodiments, the color image is a 3 dimensional representation of the lungs, wherein each data point in the representation is located at a location corresponding to a location of the matched pair of voxels in the patient's lungs.

Some methods further include classifying lung tissue at the location of the matched pairs of voxels, by using the calculated continuous probability, as being normal or being abnormal. For example, the method may include classifying the lung tissue which is abnormal as having air trapping only without emphysema, or as having emphysema.

Various embodiments include systems for performing the methods. In some embodiments, the system is a system for assessing and displaying lung function using a first set of lung volumetric images obtained at inspiration and a second set of volumetric images obtained at expiration from a patient. The system may include a display, a processor, a computer readable medium, and software executable by the processor. The software may be configured to process the first and second set of images to identify known anatomical structures of the lungs, register the first set of images to the second set of images to match voxels of the first set of images to voxels of the second set of images as matched pairs of inspiratory and expiratory voxels, calculate a continuous probability of a lung characteristic at a location of the matched pairs of voxels, generate an image depicting a set of data points, wherein each data point represents the calculated continuous probability of each of the matched pairs of voxels or a different value derived from the continuous probability of each of the matched pairs of voxels, and present the image to a user on the display.

In some embodiments, each data point is depicted in the representation at a location corresponding to a location of the matched pair of voxels in the patient's lungs. The continuous probability of a lung characteristic may be a continuous probability of tissue destruction and a continuous probability of a ventilation deficit. The image may include a plurality of colors in a color spectrum, wherein the color of each data point is a composite of a first color component dependent upon the continuous probability of a ventilation deficit and a second color component dependent upon the continuous probability of tissue destruction.

In some embodiments, the software is further configured to calculate a probability of a tissue being normal at the location in the lung corresponding to each matched pair of voxels using the continuous probability of the lung characteristic. For example, the software may be configured to calculate a probability of the tissue being normal, emphysematous, and having air trapping without emphysema at the location in the lung corresponding to each matched pair of voxels using the continuous probability of the lung characteristic. The software may be further configured to use the probabilities of the tissue being normal, emphysematous, or having air trapping without emphysema to classify the tissue as normal, emphysematous, or having air trapping at the location in the lung corresponding to each matched pair of voxels. The image may be a 3 dimensional representation of the lungs using colors corresponding to the classification at the location of each matched pair of voxels.

Other embodiments include graphical user interfaces. In some embodiments, the graphical user interface if for assessing pulmonary function comprising a 3 dimensional representation of a lung of a patient. The representation may be colored to represent a continuous probability of a lung characteristic at each location in the image, wherein the probability was calculated for each location in matched pairs of voxels in patient CT images at inspiration and expiration.

BRIEF DESCRIPTION OF THE DRAWINGS

The patent or application file contains at least one drawing executed in color. Copies of this patent or patent application publication with color drawings will be provided by the Office upon request and payment of the necessary fee.

The following drawings are illustrative of particular embodiments of the invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

FIGS. 14A and B show a 3 dimensional lung map of $DPM_{Normal}$ at baseline (A) and follow up (B);

FIG. 15 is a key to the color scale used in FIGS. 14A and B;

DETAILED DESCRIPTION

Because of the complexity of the lungs and anatomical differences amongst individuals, a wide variety of factors can influence the form and severity of COPD as well as the outcomes of treatments such as an interventional pulmonary procedure like lung volume reduction. Embodiments described herein include systems and methods for analyzing and registering lung images during inspiration and expiration for improved determination of lung functional characteristics, disease probability and disease classification on a continuous basis, and creation and presentation of two dimension and three dimensional functional representations of the lungs based upon that determination. The improved characterization of the lungs and the visual representations may be used by a clinician to identify disease phenotypes, identify lung disease at specific locations, plan appropriate treatments, monitor disease status over time, and to determine the effectiveness of a treatment. It may also be used to refine lung cancer risk assessment and screening recommendations.

The methods described herein include analysis of volumetric lung images at inspiration and expiration and registration of those images together on a voxel-by-voxel basis. The differences in the matched locations of the images at inspiration and expiration can then be used to characterize the lung at each voxel location on a continuous basis, which information can be used to assess the function of the distinct locations within the lungs and to characterize their disease probability. This information can further be presented to clinicians using images that enable the clinician to easily visualize and understand the functional status and disease pattern in the lungs of the patient at each voxel location.

The volumetric images may be patient images or imaging data produced by CT scans such as MDCT scans, MRI scans, PET scans, or other volumetric images, for example which may be obtained using the appropriate imaging machine. Therefore, while this application may refer to CT generally, or to quantitative CT measurements, it should be understood that other imaging modalities may also be used and embodiments of the invention are not limited to CT based measurements.

Figure 1:
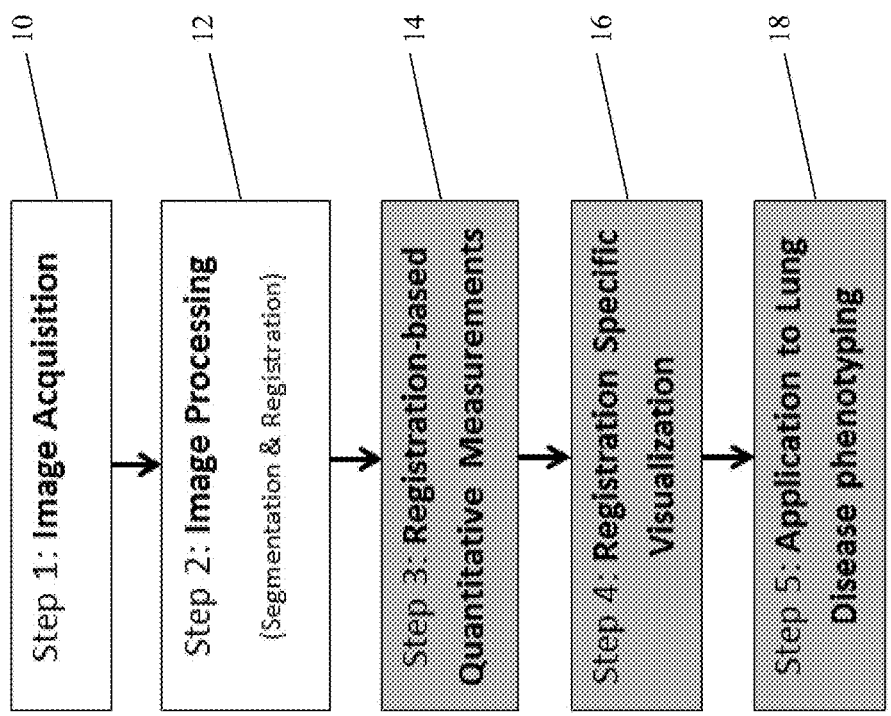
FIG. 1 is a flow chart of a method of determining a lung disease phenotype.

One method of assessing lung characteristics and classification into lung disease state and phenotype is shown in flow chart shown FIG. 1. The method may begin with image acquisition in step 10 using an imaging machine. The images may include at least two sets of volumetric images of the lungs of a patient at two different levels of lung inflation, such as breath hold images at full-inspiration and at end-expiration (full expiration). In step 12, the images are processed. The image processing step may include segmentation and registration of the lungs. For example, image processing may include segmenting the lungs into anatomical structures, such as airway segments, and extracting the vessels and fissures using known segmentation techniques. An example of a system for image processing which may be used in various embodiments and for identifying and extracting fissures is described in U.S. Pat. Pub. No. 2014/0105472 and may be used in image processing. A "lung mask" may be applied to the lung images to remove the chest wall around the lungs by considering the possible sliding motions along the lung chest wall during image processing.

Image registration may be performed using a registration algorithm to co-register the inspiration and expiration image sets, matching each voxels of the images in one set to the voxels of the corresponding location in the lungs in the other image set. For example, the algorithm may be used such as a diffeomorphic Demons image registration framework as described in T. Vercauteren et al., "Diffeomorphic demons: efficient non-parametric image registration," Neuroimage, Vol. 45, pp. 561-72, March 2009 and in B. B. Avants, et al., "Symmetric Diffeomorphic Image Registration with Cross-Correlation: Evaluating Automated Labeling of Elderly and Neurodegenerative Brain," Mid. Image Anal., Vol. 12, no. 1, pp. 26-41, 2008. The deformation may be described using a voxel-based displacement field, which allows a large degree of freedom to recover locally fine and globally large deformations. In order to account for intensity changes between the images to be registered to each other, the algorithm may utilize the local information of intensity patterns. In addition, the extracted vessel and fissure structures may be used to enhance the images in order to improve the registration accuracy, such as by using only existing portions of fissures if the fissures are incomplete. In some embodiments, the registration is performed automatically, without clinician input, other than instructing the system to perform the registration. In some embodiments, the system may perform the registration and then request confirmation from the clinician. In some embodiments, the clinician may be able to input markers at corresponding locations in each set of images to aid the registration process, for example as part of a manual correction process, such as during the manual confirmation step.

Figure 2:
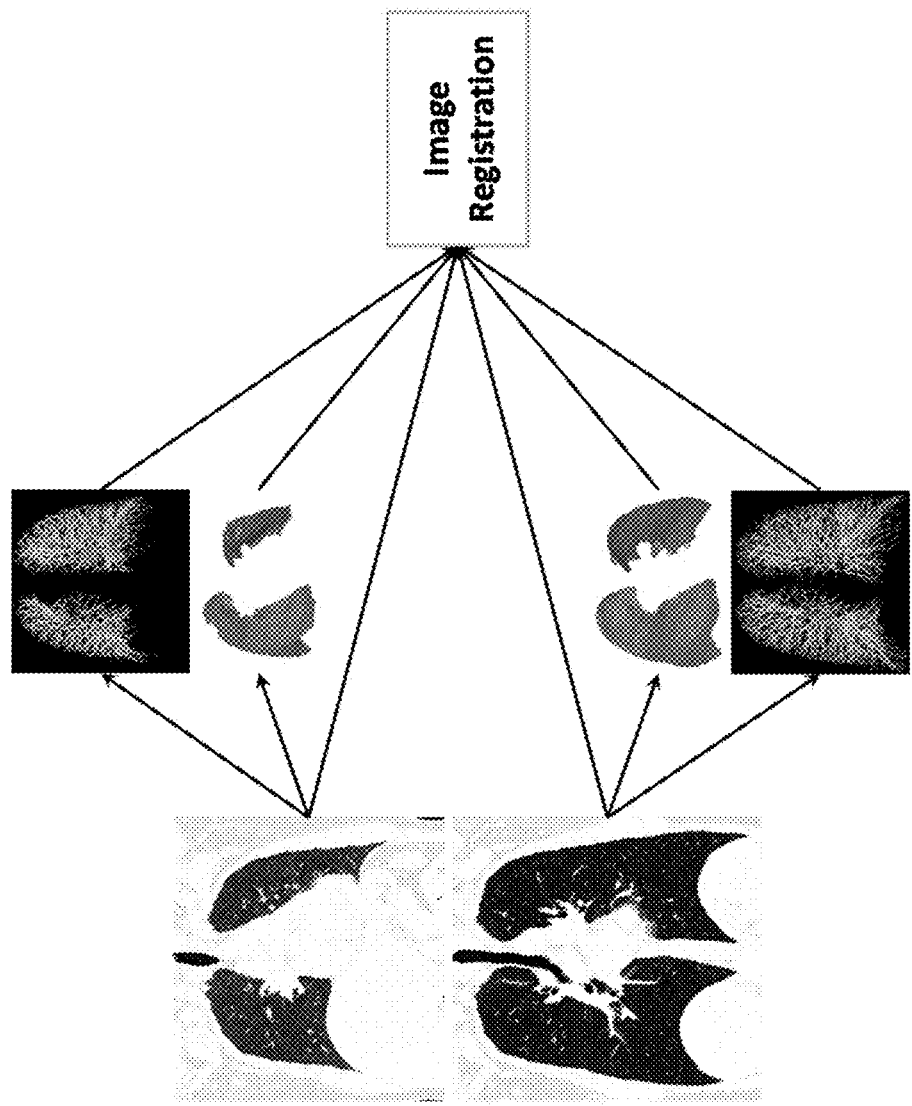
FIG. 2 is a representation of the process of image registration.

A representation of the image processing and co-registration process is shown in FIG. 2. Beginning with a set of full inspiration CT images and a set of end expiration CT images, represented by the pair of single lung images shown on the left of FIG. 2, the vessels, airways, and fissures are extracted from each set of images. This is represented by the 3 dimensional images of the vessels and of the fissures (with blue representing existing fissure and green representing missing fissure) in the center of the FIG. 2. These extracted vessels and fissures from each set of images are then used to guide the intensity-based registration, as shown at the right of FIG. 2 in the box marked image registration.

Once the two sets of volumetric images have been registered together, registration-based quantitative measurements can be obtained in step 14. These quantitative measurements may be obtained from the matched set of images on a voxel-by-voxel basis to characterize the lung at each the location of each voxel using measurements as inspiration as compared to expiration.

For example, the quantitative measurements may be used to determine the presence of or quantify lung characteristics at locations corresponding to each voxel throughout the lungs. For example, lung functional characteristics such as ventilation deficits and/or tissue destruction at voxel locations throughout the lungs can be identified and/or estimated. This may be done by comparing the HU of the each voxel in the set of images in the full inspiration scan to the HU of the corresponding voxel in the full expiration scan, as identified by the registration process. Rather than using fixed cut off values for this characterization, a continuous spectrum of values may be obtained which more accurately quantifies the lung characteristic at each location. As a result, this method is more sensitive to subtle abnormalities and changes than methods employing thresholds.

In some embodiments, a disease probability measure may be determined for each location in the lung corresponding to a voxel. The disease probability measurement may be a numerical probability that a disease or condition is present, such as the presence of a ventilation deficit and/or lung tissue destruction, which may also be referred to as parenchymal damage. The disease probability measure can include the probability of the tissue being normal, since it is inversely related to the probability of it being diseased.

For example, when the registered image sets are MDCT images, the MDCT intensity value measures the density of the object, and typical values may be taken as indicating air and tissue, such as $HU_{air}=-1000$ for air and $HU_{tissue}=55$ HU for tissue (parenchyma and blood vessels). Alternatively, the HU values used for air and tissue may be determined using the image sets, such as by sampling the center of the trachea to determine the HU value for air and in the aorta for the HU value for tissue, to be used for correction in case the imaging device was out of calibration.

In various embodiments, it is assumed that the lung is primarily composed of two components, tissue and air. The fractions of air ($\alpha$) and tissue ($\beta$) at one given voxel in the image can be estimated from the image intensity value (I), which is the measured HU for the voxel, using the following equations, for example:

$$\alpha = (HU_{tissue} - I)/(HU_{tissue} - HU_{air})$$

$$\beta = (I - HU_{air})/(HU_{tissue} - HU_{air})$$

The functions $f$ and $g$ can be used to estimate the lung characteristics of ventilation deficit and structure destruction, respectively, in each pair of matched voxels to generate a continuous value for each. For example, simple definitions of functions $f$ and $g$ can be expressed as a function of the fractions of air and the fractions of tissue in inspiratory and expiratory scans:

$$f = \alpha_{insp} - \alpha_{exp}$$

$$g = (\omega \beta_{exp} + \beta_{insp})/(\omega + 1)$$

where $\omega$ is a weight coefficient introduced to take into consideration the difference of noise levels in the two images (inspiratory, expiratory). In this example, function $f$ is simply defined as the air fraction changes between the paired voxels while function $g$ is defined as the weighted tissue fraction in the paired voxels.

In the definition of $f$ above, ventilation was computed irrespective of the underlying tissue type. However, accuracy can be improved by taking into consideration the tissue fraction of the voxel. That is, a voxel with a higher tissue fraction may play a lesser role in ventilation. The function used for $f$ can therefore optionally be modified to the following equation, in which a varying weight is introduced which is defined as a function of the tissue fraction:

$$f = e^{-g}(\alpha_{insp} - \alpha_{exp})$$

As described above, the functions of $f$ and $g$ may be simply defined from the fractions of air and tissue. However, other definitions can be used instead or combined with the current ones. For example, ventilation measurements derived from the Jacobian value and/or changes in local air volume can be used for $f$. Similarly, gradient-based measurements can be introduced for $g$. Other lung values may also be calculated on a continuous basis using the matched pairs of voxels, such as by using the intensity measurements of the matched pairs of voxels.

Various embodiments for determining the probability of a ventilation deficit are based on the observation that the smaller the change in air fraction, the larger the probability of ventilation deficit. That is, if the level of air fraction is similar between the two scans, the probability of a ventilation deficit is maximal, pointing to a lack of lung compliance (or potentially, as a source of error, due to the scans not being full inspiratory and expiratory scans, such as if there was a lack of proper breathing coaching or a lack of patient compliance when the images were obtained). Similarly, various embodiments for determining the probability of tissue loss or destruction are based on the observation that a pair of voxels is most likely to indicate a tissue destruction at the corresponding location in the lung if the weighted tissue fraction is close to 0 and therefore indicative of only air and little or no tissue in the voxel. As such, the likelihood of a ventilation deficit or a tissue destruction may be determined using a comparison of the intensity measurements of the images at each voxel, relative to each other, on a continuous basis, rather than using a cut-off value for intensity measurements.

The probability of a ventilation deficit and of tissue destruction at each voxel location may be estimated mathematically using the co-registered voxels from the two sets of volumetric images by any appropriate method. For example, in one embodiment, the deficit in ventilation may be calculated as $$VentDef = e^{-f/\sigma_v}$$

and structural destruction may be calculated as $$StructDest = e^{-g/\sigma_s}$$

where $\sigma_s$ and $\sigma_v$ control the sensitivity and can be determined by simulations. An exponential decay function may be used, or other similar monotonic decreasing functions with different rates of decay such as Normal or Cauchy functions. Other methods of calculating the probabilities of these or other lung characteristics may alternatively be used to generate continuous values on a voxel-by-voxel basis.

The voxel-by-voxel probabilities of the characteristics ventilation deficit and tissue destruction or other lung characteristics, which may be determined as described above or using a different method, may be used to derive a disease probability measure (DPM) for each lung location corresponding to a matched pair of voxels. For example, at least three states may be of particular interest to characterize the health of the lung tissue: normal tissue, emphysematous tissue, and tissue having air trapping without emphysema (referred to as "air trapping"). Normal tissue may be expected to have low probabilities of both ventilation deficit and tissue destruction. In contrast, emphysematous tissue may have a high probability of both ventilation deficit and tissue destruction, while in tissue in which air-trapping alone is present there may be a high probability of ventilation deficit but low probability of tissue destruction. These observations may be used to calculate a disease probability measurement for each matched pair of voxels using the functions listed below, for example.

$$DPM_{normal}=(1-VentDef)\times(1-TissLoss)$$

$$DPM_{Emph}=VentDef\times TissLoss$$

$$DPM_{AirTrap}=(VentDef)\times(1-TissLoss)$$

$$DPM_{EmphWoAirTrap}=(1-VentDef)\times(TissLoss)$$

$DPM_{normal}$ represents the probability that the tissue is normal. $DPM_{Emph}$ represents the probability that emphysema is present. $DPM_{AirTrap}$ represents the probability that air trapping is present (that is, air trapping only without emphysema). It should be noted that the class $DPM_{EmphWoAirTrap}$, or the probability of emphysema without air trapping, should not be observed since tissue damage due to emphysema is typically associated with trapped air. Therefore, this class may be considered fictitious and may be excluded in various embodiments. These disease probability measurements provide continuous quantitative predictions of lung disease at each location in the lung corresponding to a matched pair of voxels. This continuous quantification may be particularly useful for the detection of disease at early stages where the use of simple cut off values would not be able to detect more subtle abnormalities associated with early disease. This also makes it well suited for monitoring of subtle progression of lung disease over time, which may not be detected by methods which use cut off values rather than continuous calculations.

In some embodiments, it may be useful to convert the continuous disease probability measurement scores into a tissue classification scheme, which may classify the lung tissue into normal, emphysematous, or having air trapping only without emphysema. This may be done using an approach which is similar to the posterior probability-based clustering method, but other unsupervised methods can also be used. Each voxel location may be classified or categorized into one of three tissue states (normal, emphysematous, and air trapping only without emphysema) using the disease probability measures. The percentage of the area of the lung for each slice, or the percentage of the volume of the entire lung or of a portion of the lung, classified into each state can be computed and provided to the clinician. In some embodiments, additional states may be identified and included in the categorization. For example, the abnormal states (emphysema and air trapping) may each be further classified according to the severity of the abnormality, such as into levels such as mild, moderate and severe for each abnormal state.

The voxel-by-voxel measurements and calculations of lung characteristics obtained in step 14 may be used to create one or more visual representations of the lungs in step 16. For example, the visual representations may be two dimensional or 3 dimensional representations of the lungs, with color variation used to represent the continuous scale of values for the characteristics. The color corresponding to the values for each matched voxel may be shown at the corresponding location in the visual representation of the lungs in a manner that can be easily understood by the clinician. The registration-based quantitative measurements of lung characteristics of step 14 may further be used for lung disease phenotyping in step 18 based upon disease probability measures, for example.

Disease phenotype identification in step 18 may be applied to subjects in numerous ways. For example, the phenotype may be used to identify most likely future outcome and for making treatment decisions. For example, one can use the registration-based quantitative measurements of lung characteristics to identify asymptomatic or at risk subjects who are likely to develop COPD or those subjects likely to have a rapid decline in lung function over time. In another example, the subjects who are most at risk for lung cancer can be identified based on their phenotypes, and appropriate lung cancer screening recommendations can be made. Lung disease phenotyping using registration-based quantitative measurements could also be useful to improve patient selection and treatment planning for procedures such as lung volume reduction procedures or bronchothermoplasty, such as for severe asthma. For example, if a subject has an air-trapping phenotype based on the registration-based measurements, the identification of this phenotype could be used to decide what treatment should be recommended, if any, and where and how the treatment should be applied.

Figure 4:
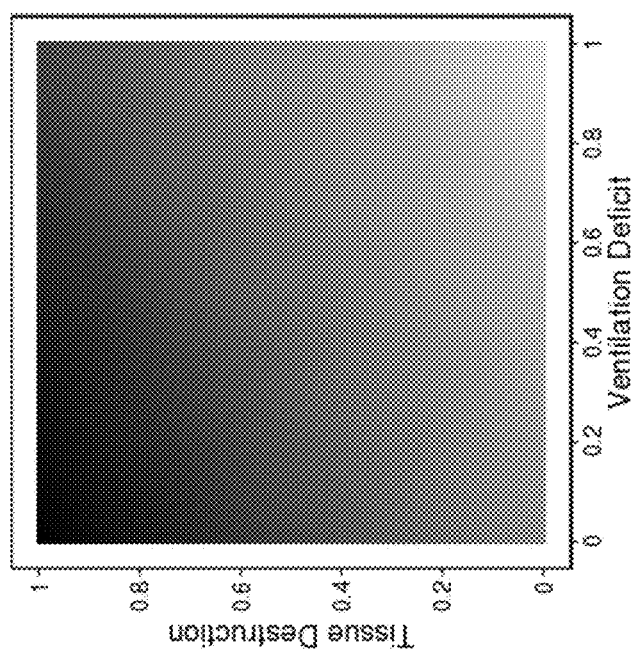
FIG. 4 is a colored scale for characterizing the lung characteristics of ventilation deficit and tissue destruction on a continuous basis.

In some embodiments, a color code scheme may be used for the representation of the lungs, where different colors spectra correspond to different probability values of lung characteristics at each voxel location. In some embodiments, two color spectra may be used to correspond to two measurements of lung characteristics. For example, a red-green-blue color scheme may be used in which the calculated ventilation deficit shown as the red component and the calculated structural destruction is shown as the green component at each matched voxel location. An example of such a color scheme is shown in FIG. 4. The x-axis is the spectrum of ventilation deficit with a score from zero to 1, with zero being normal, and 1 being a complete ventilation deficit. Similarly, the y-axis is the spectrum of tissue structure destruction with a score from zero (normal) to 1, complete tissue structure destruction.

Referring again to FIG. 4, a ventilation deficit of 1, with no tissue structure destruction, is represented by yellow and indicates a clinical state of air trapping only, with no emphysema. A tissue structure destruction of 1, with no ventilation deficit, is represented by black and indicates a clinical state of emphysema only with no air trapping (though this is not expected to occur clinically because it is believed that emphysema does not occur without air trapping). Finally, the presence of both tissue structure destruction and air trapping is represented by red and indicates a clinical state of emphysema with air trapping. Other color schemes or visual representation schemes could alternatively be used. Likewise, the color schemes or visual representation schemes could be used to represent measurements of characteristics other than tissue structure destruction and ventilation deficit.

The color scheme selected to represent the value of the continuous probability of the lung characteristics may be used in a visual representation of the lungs, such as a 2 dimensional or 3 dimensional representation. The color corresponding to the probability value of the matched voxels for each location in the lung may be used in the visual representation of the lung at each voxel location. For example, because the lung is a complex 3 dimensional structure, in order to present the lung to the user on a 2 dimensional format such as a display (such as a computer screen) a 3 dimensional representation of the lungs may be provided by showing a series of image slices, akin to CT image slices, one at a time and allowing a user to move from one image to the next to progress through the volume of the lung.

Figure 5:
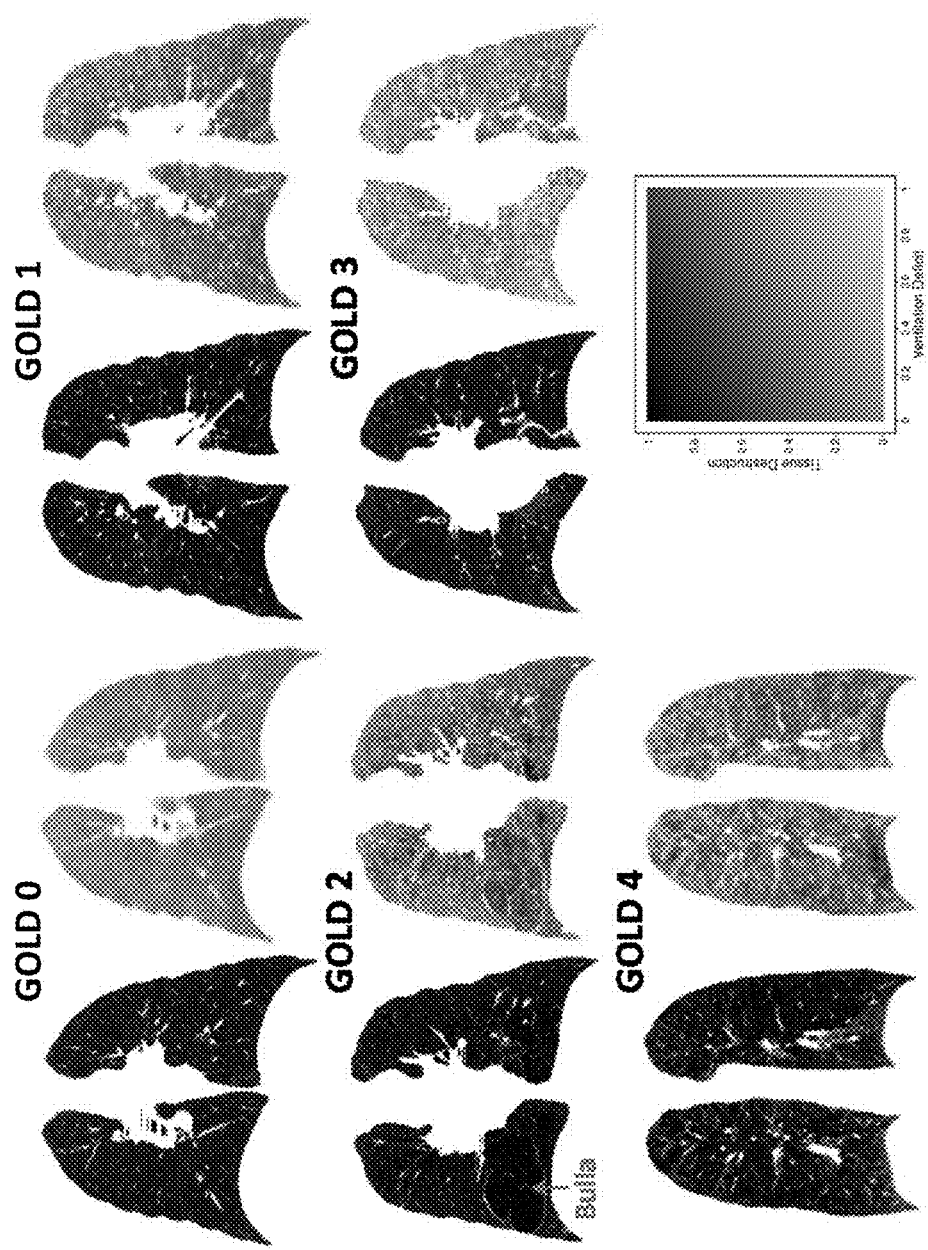
FIG. 5 displays CT images and corresponding 3 dimensional representations of lung characteristics from 5 patients with GOLD stage 0 to GOLD stage 4 COPD.

Examples of such 3 dimensional visual representations are shown in FIG. 5, in which the 3 dimensional representations of the probabilities of lung characteristics of 5 patients are shown, along with a corresponding CT image, as well as a key to the color scheme used in the 3 dimensional visual representation. The patients from whom the images were obtained and for whom the 3 dimensional visual representation are shown had GOLD stages from zero to 4. As can be seen, the coloration of the locations of the lungs corresponding to each voxel of the CT image in the GOLD zero patient is mostly green, and shifts to include increasing amounts of yellow (corresponding to ventilation deficit) and red (corresponding to emphysema with air trapping) as the GOLD stage increases. At GOLD stage 4, the 3 dimensional representation of the patient's lung includes the highest amount of red, as is expected for a patient with this category of disease. The corresponding CT image, to the left of each 3 dimensional representation, shows a CT image slice at the same location as the slice of the 3-dimensional representation. Presenting these images together may be useful to help the physician interpret the 3-dimensional representation. For example, in the GOLD stage 2 patient, a large area of red (corresponding to emphysema with air trapping) can be seen in the lower portion of the right lung in the 3-dimensional visual representation. In the corresponding CT image, it can be seen that a large bulla is present at that location. Various embodiments may therefore provide a clinician with a visual display including a 3 dimensional representation of the lungs and may further include the corresponding CT image and may also include a color scheme key or guide like those shown in FIG. 5 for a particular patient.

Figure 6:
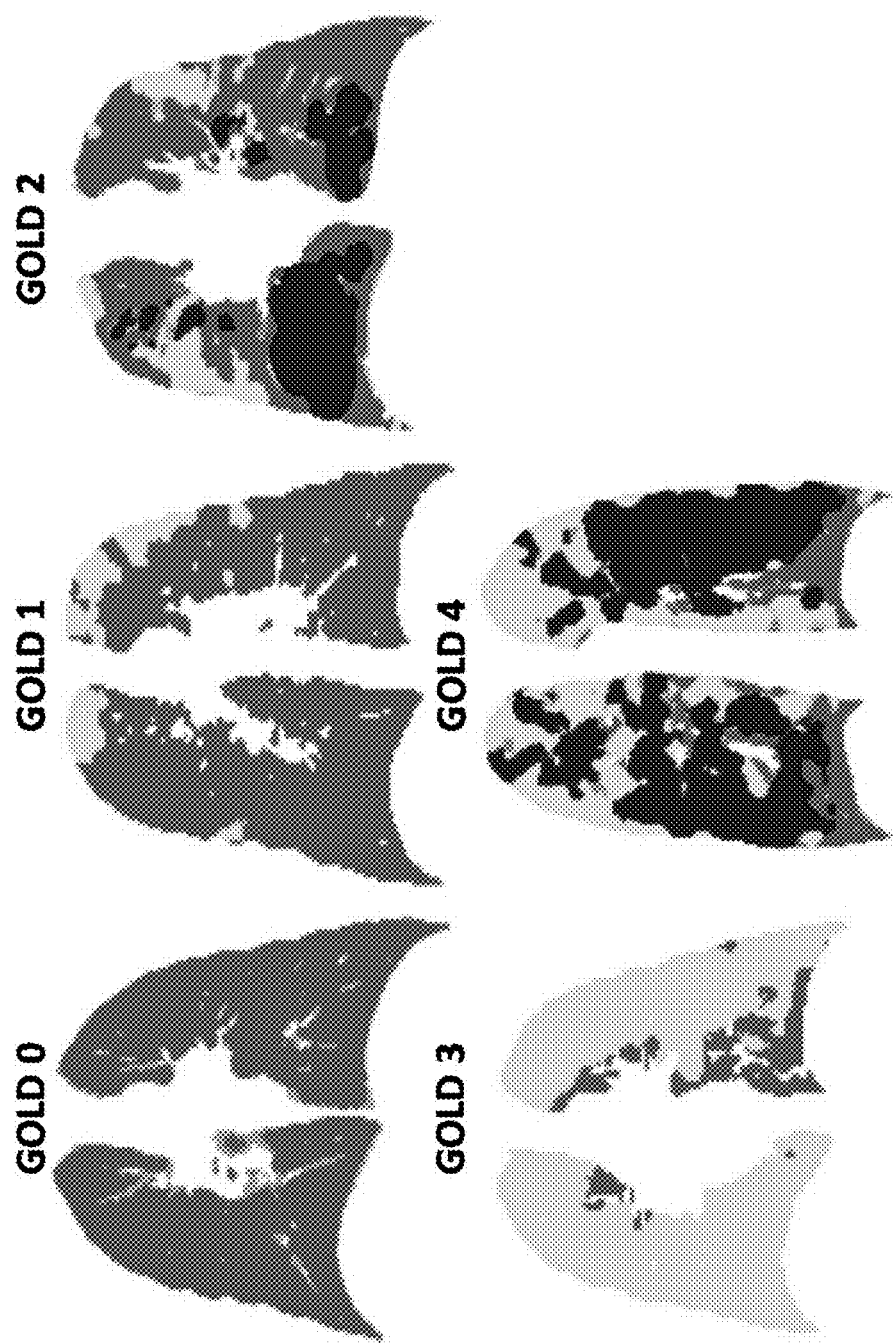
FIG. 6 displays 3 dimensional lung representations colored to show disease probability for the same 5 patients.

In some embodiments, the 3 dimensional visual representation of the lungs may show by color the classification of each voxel location into each state as determined using the disease probability measurements as described above. In such embodiments, each state may be represented by a particular color. An example of a 3 dimensional representation of the lungs including such a classification of the tissue into states is shown in FIG. 6. In this figure, the 3 dimensional lung representations of the tissue states are shown for the same GOLD stage zero to 4 patients as in FIG. 5. However, rather than a spectrum of colors as shown in FIG. 5, in this type of representation the use of a classification reduces the number of colors to one color per classification state. In this example, green represents normal lung, yellow represents air trapping, and red represents emphysema. A bulla is shown in the right lung of the GOLD 2 patient. Serious air trapping is shown in the GOLD 3 patient, and a predominance of serious emphysema is shown in the GOLD 4 case.

Figure 7:
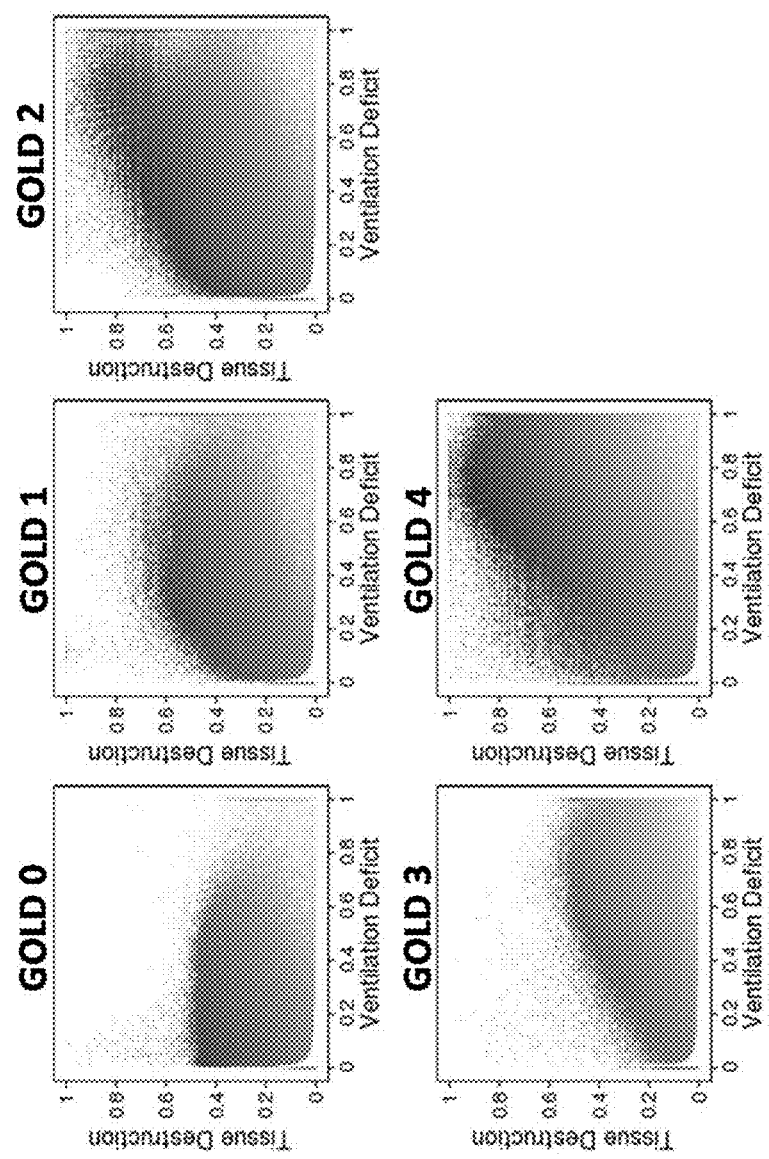
FIG. 7 displays scatter plots of the voxel-by-voxel lung characteristics for the same 5 patients.
Figure 8:
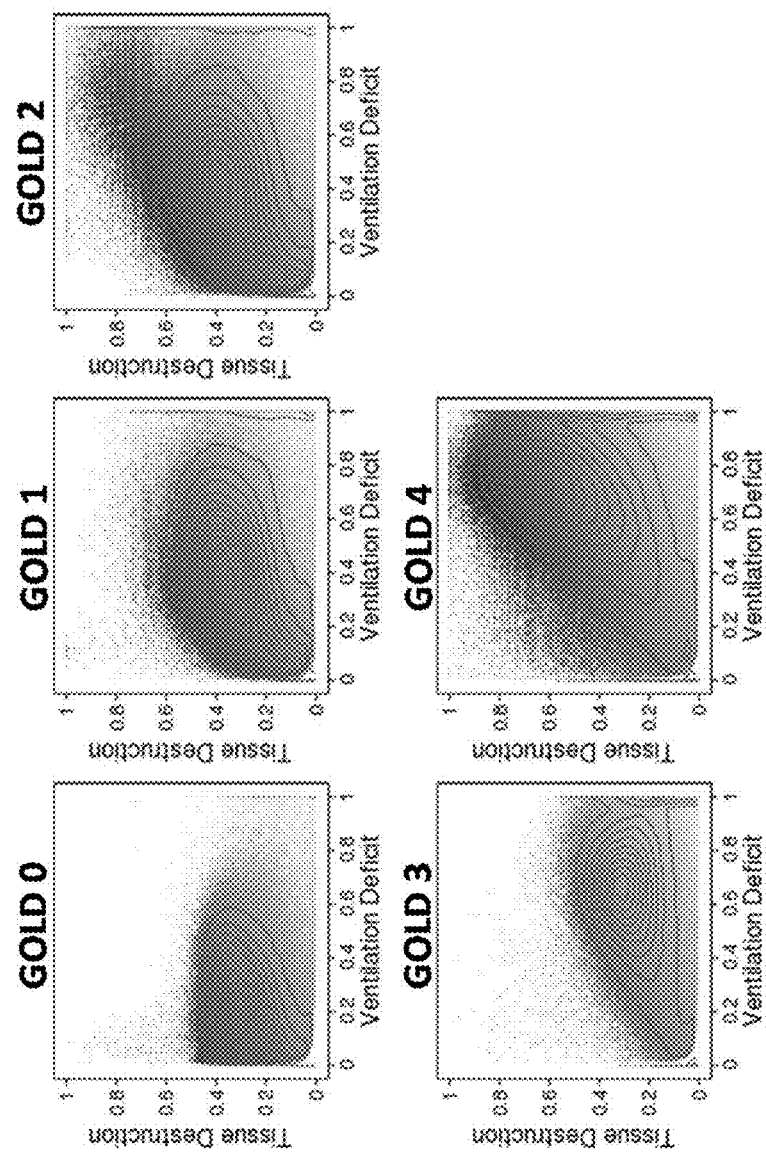
FIG. 8 displays the scatter plots of FIG. 7 including a lung print.

Another alternative display is shown in FIG. 7, in which the data from the same 5 patients from FIGS. 5 and 6 is shown in a different format. This figure shows examples of a two dimensional display of the point values for each paired voxel of the probability of the lung characteristics, with ventilation deficit on the x-axis and the tissue structural destruction on the y-axes, using the same color scheme described above and shown in FIG. 4. The result is a scatter plot type of display. It can be seen that in the GOLD 0 patient, the values are clustered close to the lower left zone (corresponding to normal) and green in color for nearly all paired voxels, while the values increasingly are dispersed up and to the right into the abnormal areas as the GOLD level increases to 4. In FIG. 8, the same type of two dimensional data display is shown for the same 5 patients, but further including contour lines to depict the quantity of values at each coordinate location, in the nature of a 3-dimensional topographic display. Each contour line connects points having equal numbers of voxels. The result is a sort of "lung print" which allows a user to understand the distribution and density of data points, corresponding to each matched pair of voxels, for each lung characteristic. Various quantitative measures can be extracted from these 2 dimensional topographic maps, such as the number of peaks, the location of peaks, the slope and curvature of the 3 dimensional histogram, the distance between contours (topographic lines), and the length of contours. Similarly, wavelet technology, used for fingerprint recognition, may be used to characterize and extract the unique lung signature of an individual based on the lung topographic map. These images and the extracted values may be provided for a clinician as part on the display for characterizing the patient's health as well as for monitoring the evolution of the patient's lungs over time and for matching (categorizing) an individual with a series of other individuals with identical or similar lung health in a given lung image database. The images and derived data may also be used by a clinician for characterizing an individual's disease status and phenotype. For example, in the GOLD 3 patient, it can be seen that the patient has an air trapping dominant form of disease, while the GOLD 4 patient has an emphysema dominant form of disease.

Figure 9:
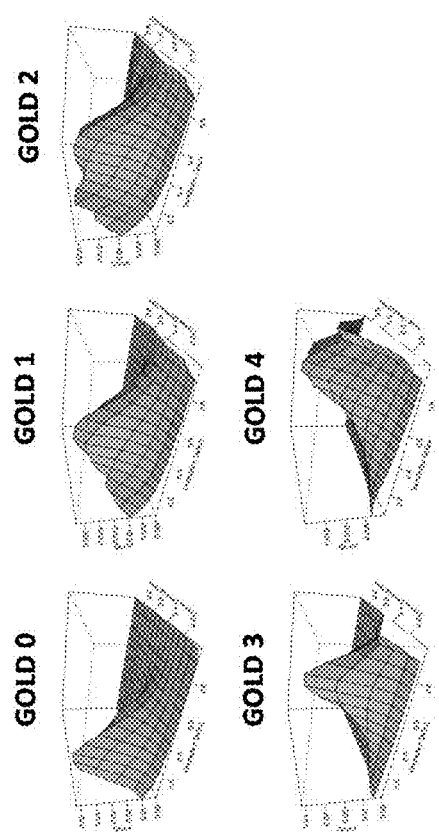
FIG. 9 displays the voxel-by-voxel lung characteristics of the same 5 patients in a 3-dimensional view.

A similar concept is shown in FIG. 9, but using a 3 dimensional type of image rather than topographic lines. Although these images are shown in black and white, a color spectrum like that of the previous image may alternatively be used. As in FIGS. 7 and 8, the calculated probability values for ventilation deficit verses tissue destruction are shown for each pair of matched voxels are displayed for the same 5 exemplary patients. However, a $3^{rd}$ dimension (z-axis) is added to show the number of voxels for each coordinate location on the ventilation deficit/tissue destruction axis. There is a shift of the location of the main peak towards more emphysema with air trapping as the GOLD stage increases.

Figure 3:
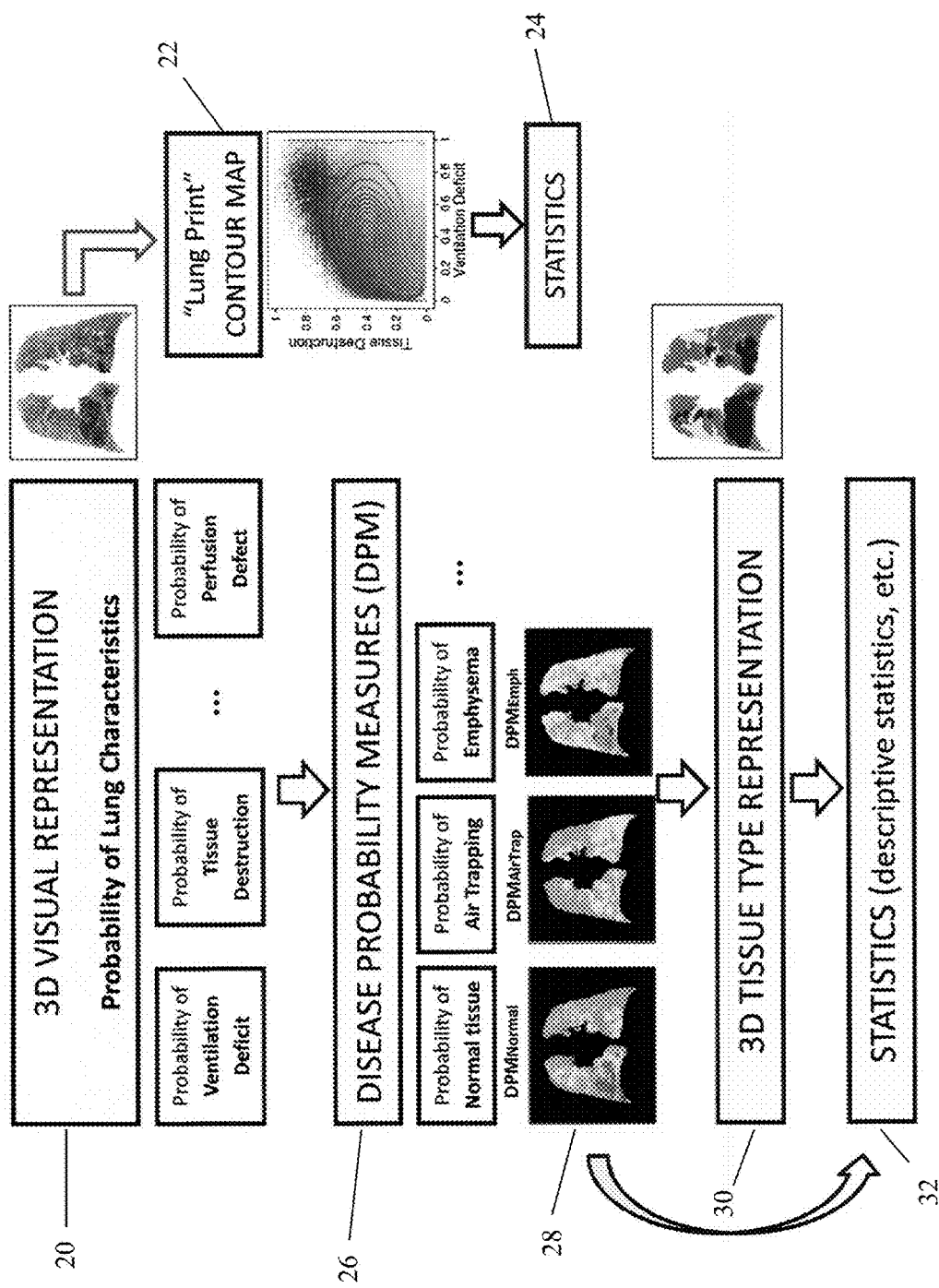
FIG. 3 is a representation of methods of generating visual representations and statistics using the probability of lung characteristics.

An alternative representation of a process and the various steps which may be included in various embodiments is shown in FIG. 3. After image acquisition and processing and determination of registration based measurements of continuous probabilities of lung characteristics, the continuous probability of the lung characteristics at each voxel location may be presented in a 3 dimensional visual representation in step 20 of FIG. 3 (which may be considered one type of registration specific visualization of step 16 of FIG. 1). The lung characteristic shown in the 3 dimensional visual representation may include characteristics such as the continuous probability of a ventilation deficit and/or tissue destruction. Other registration based characteristics, such as the probability of a perfusion defect, may also be determined as continuous probabilities and presented in a 3 dimensional visual representation. The lung characteristic data used for the 3 dimensional representation may also be used to create a 2 dimensional image such as a contour map in step 22 and may be used to generate statistics regarding the lung characteristic data in step 24.

The lung characteristic data used to generate the 3 dimensional visual representation in step 20 may be further used to calculate disease probability measures in step 26, such as the probability of normal tissue, of tissue with air trapping only, or of emphysema, at each voxel location. Any one or more or all of the disease probabilities may be displayed as 3 dimensional visual representations in step 28. In addition, the disease probability measures may be used to categorize the tissue at each voxel location into a tissue type, such as normal, air trapping only, or emphysema, and this classification may be used to generate a 3 dimensional visual representation of the lungs showing the tissue classifications in step 30. Finally in step 32, the data relating to lung characteristics, disease probability measures, and tissue classification can be used to generate statistics. These statistics may be useful for understanding disease patterns across patients for predicting outcome and for selecting treatments and screening programs for individuals with similar statistics. For example, descriptive statistics such as histograms, mean, median, standard deviation, etc. can be determined for each disease probability (e.g. the probability of the tissue being normal, having air trapping, or having emphysema). Descriptive statistics can also be determined for the disease classification of the tissue, such as the percent of each classified tissue type (such as normal, air trapping, or emphysema) for the entire lung or separately for distinct portions of the lung such as the lobes, the sublobes, etc. More sophisticated statistics can also be generated from the data produced as described herein.

The lung registration and characterization may be performed by a system for lung characterization and visualization. The system may further be used for monitoring patients over time. The system may further perform treatment planning, such as lung volume reduction treatment planning system. In some cases, the system may perform a lung cancer risk analysis and/or recommend a lung cancer screening regimen.

The system may include a processor, such as a processor in a computer, and may also include a visual display such as a monitor or other display screen to present visual displays to a user such as a clinician. The system may also include instructions included in software, stored in memory of the system, and operable on the processor. The software may include instructions for the processor to perform the various steps and methods described herein, including instructions to receive patient data including volumetric imaging data including inspiration and expiration image sets, process and segment the images, register the image sets to each other, analyze the paired voxels of the registered images including characterizing the paired voxels on a continuous scale of tissue destruction and ventilation deficit, calculate a probability of normal tissue and of diseased tissue (emphysema or air trapping) at each paired voxel, categorize each voxel based upon the continuous measurements into normal and abnormal tissue (emphysema or air trapping), and register sets obtained at different times, and calculate in image sets across time. The software may further include instructions to display images including three-dimensional images of the pulmonary tree and functional displays of the lungs based upon the continuous measurements. The software may further include instructions to receive clinician approval of an image registration, or input from a clinician to refine or repeat the image registration based on anatomical locations marked by the clinician in each image set. In some embodiments, the system may calculate a lung print as described above. In some embodiments, the system may display a lung cancer risk or recommendations for lung cancer screening for a patient. Some embodiments may use a 3D pulmonary imaging software such as the APOLLO quantitative pulmonary imaging system software, available from VIDA Diagnostics, Inc., which may be modified or combined with other software to perform the functions described herein.

Examples of the embodiments may be implemented using a combination of hardware, firmware, and/or software. For example, in many cases some or all of the functionality may be implemented in executable software instructions capable of being carried out on a programmable computer processor. Likewise, some examples of the invention include a computer-readable storage device on which such executable software instructions are stored. In certain examples, the system processor itself may contain instructions to perform one or more tasks. System processing capabilities are not limited to any specific configuration and those skilled in the art will appreciate that the teachings provided herein may be implemented in a number of different manners.

Various embodiments may allow the clinician to visualize and interact with the three-dimensional representations of the lungs and the two-dimensional images. For example, the three-dimensional model and the associated two-dimensional images may be presented in a graphical user interface on a visual display. The user may interact with the graphical user interface, such as by selecting a button, icon, and/or one or more locations on the images or the model or elsewhere using a mouse, stylus, keypad, touchscreen or other type of interface known to those of skill in the art. The creation of the three-dimensional representations may be performed by the system including a processor with software instructions to perform this function as well as software to permit a user to interact with the graphical user interface, to calculate and display desired data and images, and to perform the other functions described herein. The system may further include the visual display on which the graphical user interface is displayed. The three-dimensional representations and two-dimensional images may be provided to a user (such as a clinician or researcher) as a graphical user interface on a visual display, which may be a computer screen, on which the images and data may be manipulated by the user.

The various 2 dimensional and 3 dimensional depictions of lung characteristics, disease probability, state, and change over time described herein may be shown as components of a graphical user interface implemented by the system on a display to allow a clinician to understand and monitor the lung disease in a patient. The graphical user interfaces may include additional features as well, such as three dimensional images of the airways such as those described in U.S. Pat. Pub. Nos. 2014/0105472 and 2012/0249546, the disclosures of which are hereby incorporated by reference, for example. The display of the airways may further include airway measurements such as wall thickness, wall, area, luminal area, and other measurements which may be numerically displayed, which may be obtained for the medium sized airways, for example. In some embodiments, the graphical user interface may include images and related measurements like those shown in FIGS. 4 to 9 and 12 to 18 (described below) which provide functional information about the small airways, as well as structural images and related anatomical measurements like the airways trees which provide structural information. In this way, the clinician can simultaneously observe both the structural and the functional characteristics of the patients' lungs.

Figure 10:
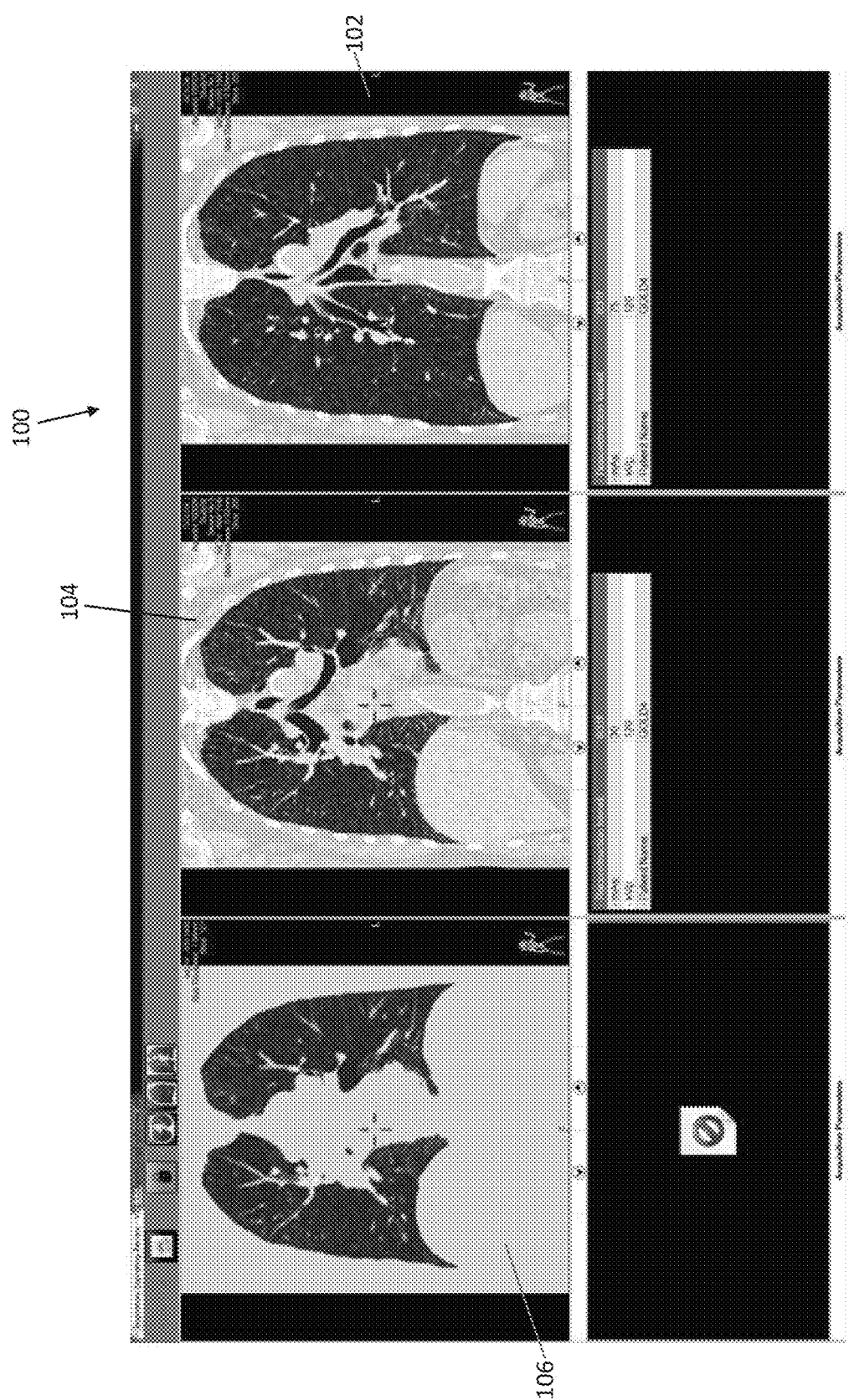
FIG. 10 shows an example of a graphical user interface for visual confirmation of lung registration.
Figure 11:
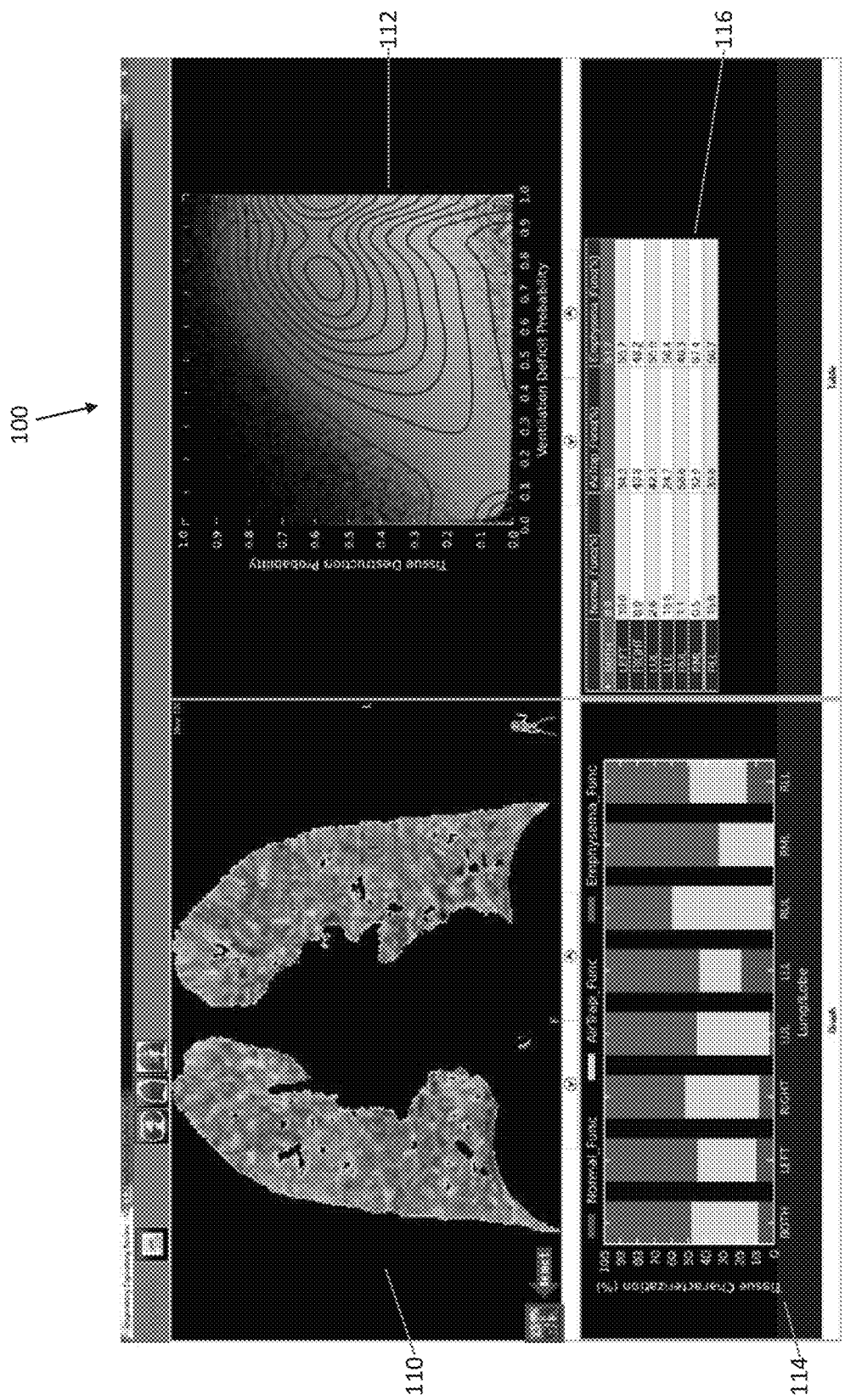
FIG. 11 shows an example of a graphical user interface including functional lung images and data and disease probability data.

Examples of graphical user interfaces which may be used in various embodiments are shown in FIGS. 10 and 11. FIG. 10 presents an example of a graphical user interface 100 that may be provided to a clinician during the step of registration of the image sets to allow the clinician to verify the accuracy of the registration if desired. In this example, the inspiratory and expiratory images 102, 104 have been correlated automatically to generate a composite image or warped image 106 of the registered lungs. Such a graphical user interface may be displayed for the clinician so that the clinician can visually confirm the accuracy of the registration process. In some embodiments, if the clinician detects an error in the registration, the system may allow the clinician to input one or more pairs of markers on each of inspiratory and expiratory images, to identify the same anatomical location on each image. These markers may then be used by the system during registration to match the corresponding locations in the inspiratory and expiratory images and to repeat the registration process with improved accuracy.

Another example of a graphical user interface 100 is shown in FIG. 11, which may be provided to a clinician after the images have been registered and the continuous functional measurements have been obtained. In one portion of the screen, a 3 dimensional lung representation 110 is shown in which a continuous spectrum of colors correlates to the probability of tissue destruction and ventilation deficit at every paired voxel location. The graphical user interface may allow the clinician to select different slices to be displayed, or different orientations (axial, coronal, or sagittal) for the 3 dimensional lung representation 110. The graphical user interface 100 also includes a two dimensional scatter plot with a lung print 112 for the entire lung. A color image key like that of FIG. 4, may also be provided showing the full color spectrum and the correlation to the probability values of tissue destruction and ventilation deficit, or the lung scatter plot, with or without a lung print, may be used for this purpose. The data obtained from the lung registration and continuous functional measurements may be used to calculate disease probability measures which may be used to classify each paired voxel into a discrete tissue state as described, which may be displayed as a 3 dimensional lung representation or in other ways. As shown in FIG. 11, the tissue state may be provided graphically for each portion of the lung separately, such as the left and right lung separately, or the lobes of the lung separately, or all of these, as shown in FIG. 11. The percentage of each classified state of the lung is shown in a bar graph 114 with distinct colors for normal, emphysematous tissue, and air trapping in each lung region. FIG. 11 also presents this information in numerical form in a chart 116. This allows easy understanding of the state of various distinct portions of a patient's lungs.

Because the probabilities that are determined under various embodiments are continuous and do not rely upon thresholds for categorization, they are well suited for longitudinal assessment of a subject, such as monitoring lung characteristics or disease state of each voxel location over time or for determining the response of the lungs to a treatment. This is because the continuous measurements and probabilities allow for the detection of subtle changes in value, such as small worsening or improvement, that are lost when threshold values are used.

Figure 12:
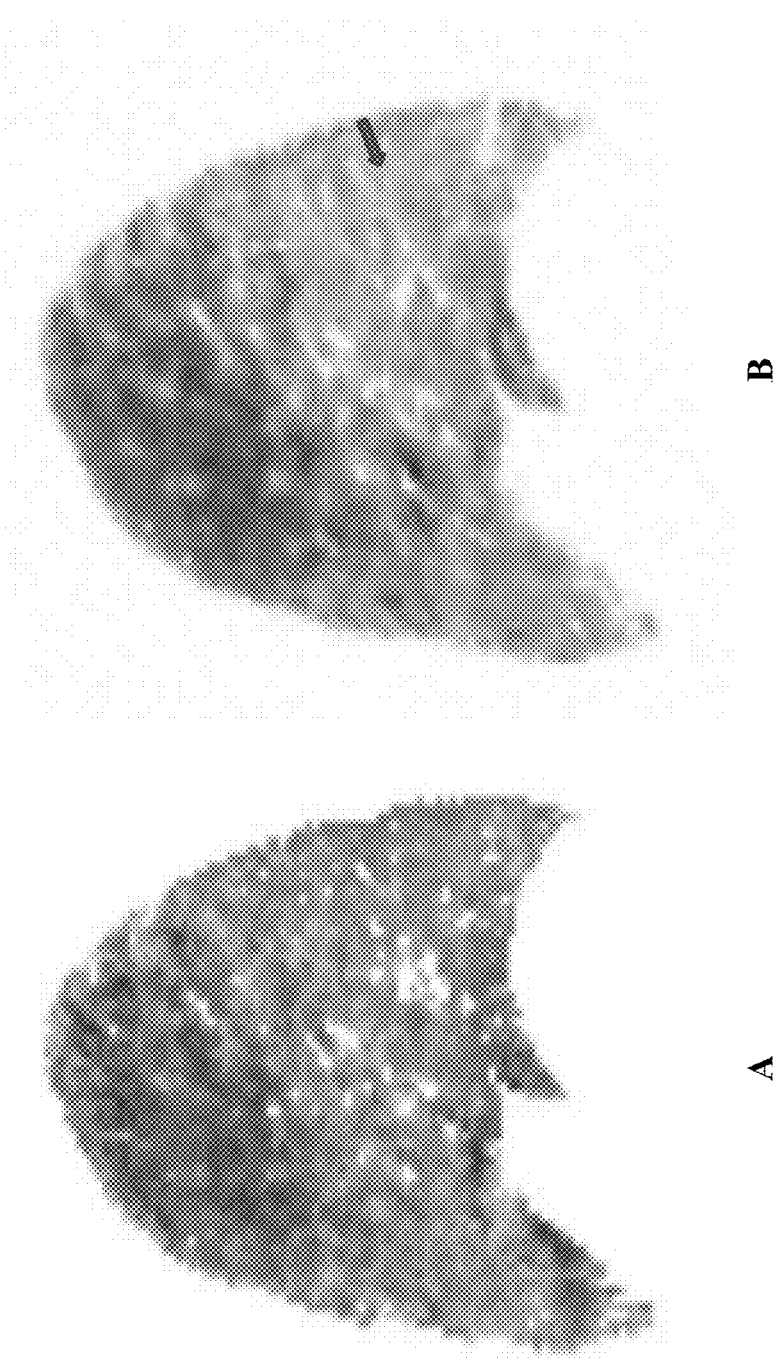
FIGS. 12A and B show a 3 dimension lung characteristic representations at baseline (A) and follow up (B)
Figure 13:
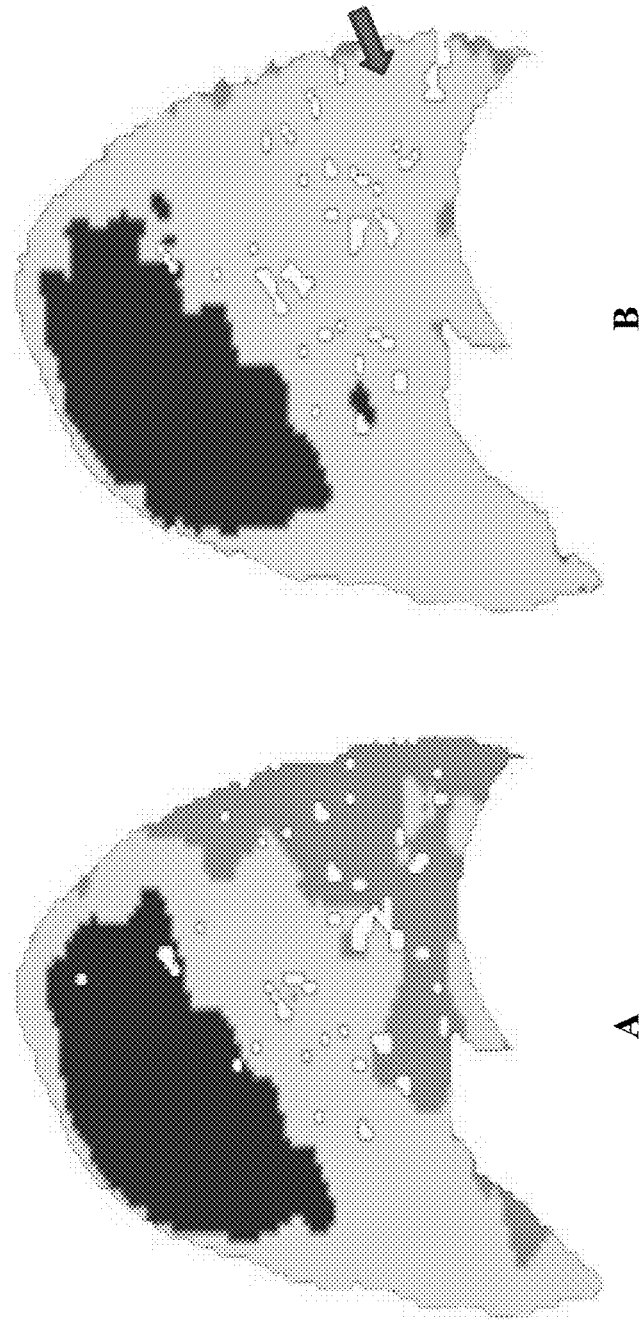
FIGS. 13A and B show a 3 dimensional lung representation showing disease classification at baseline (A) and follow up (B)

For example, a 3 dimensional representation of the probability lung characteristics at a first time and a second time, such as the 3 dimensional representation described previously above, may be displayed side by side for a clinician according to various methods. In each image, the image may be colored to represent the continuous value of the probability of one or more characteristics, such as the presence of a ventilation defect and of tissue loss, as described above. When viewed side by side, the clinician may see the difference in coloration of the image at a first time compared to a second time. An example of this type of longitudinal assessment is shown in FIG. 12, in which a 3 dimensional representation of a patient's probability of lung characteristics, in this case ventilation defect and tissue destruction, are shown side by side. A first time point is shown in FIG. 12A, at the time of diagnosis. At that time, the patient had moderate COPD (spirometry-derived GOLD-2 stage), severe shortness of breath (mMRC=3), and had a history and evidence of respiratory disease (bronchitis). A second, later time point is shown in FIG. 12B, during which time it can be seen, through the side-by-side comparison, that the lung disease has progressed. A red arrow indicates an area of change between the baseline image in FIG. 12A and the follow-up image in FIG. 12B. The use of a continuous scale of probabilities allows a comparative assessment of the magnitude of the change.

The longitudinal analysis can also be performed using a 3 dimensional representation of a classified lung states based on disease probability measures, such as those described above, at a first time and a second time. An example of such as comparison is shown in FIGS. 13A and B, in which the data from the patient included in FIGS. 12A and 12B is shown with the color indicating the state of the tissue determined by disease probability, at the same first and second time points. In these figures, the lung tissue that was categorized as normal is green, the tissue categorized as having air trapping without emphysema is yellow, and the tissue with emphysema is red. It can be seen that the patient's condition worsened at the second time point. The red arrow indicates a region of change, in which tissue that was previously categorized as normal (green) in FIG. 13A was categorized as air trapping without emphysema (yellow) in FIG. 13B.

The categorization of each voxel into a state can also be determined and presented numerically, such as in combination with the lung characteristic, disease probability, or disease state images, or representations. For example, the percent of voxels categorized as normal (DPM_NormalPerc), the percent of voxels categorized as having air trapping only (DPM_AirTrapPerc) and the percent of voxels categorized as having emphysema (DPM_EmphPerc) using the disease probability measures can be compared at two or more time points. For example, the patient shown in FIGS. 12A and B and 13A and B had the following percent of lung categorized into each state using disease probability measurements at the first time point (baseline): normal (DPM_NormalPerc) 23.4%; air trapping (DPM_AirTrapPerc) 65.3%; and emphysema (DPM_EmphPerc) 11.3%. At the second time point (follow up), the percentages were as follows: normal (DPM_NormalPerc) 3.1%; air trapping (DPM_Air TrapPerc) 83.0%; and emphysema (DPM_EmphPerc) 13.7%. These numbers show a general degradation of lung heath, with a particularly significant increase in air trapping without emphysema. The numerical values of each percent, and/or of the change in the percent of each classification, might also be displayed for the clinician.

Another longitudinal display of images, for the same patient and at the same time points as the patient in FIGS. 12A and B and 13A and B, is shown in FIGS. 14A and B. In these images, a 3 dimensional representation of the lung displays the probability that the lung is normal ($DPM_{Normal}$) at each voxel location, with the spectrum of colors used in this figure shown in FIG. 15. A $DPM_{Normal}$ score of at or near zero indicates a very low probability of normal tissue and is shown in red, while a $DPM_{Normal}$ score of at or near 1 indicates a very high probability of normal tissue and is shown in purple. A continuous spectrum of colors is used for the $DPM_{Normal}$ values between zero and one. Such a representation (or representations for other DPM values such as $DMP_{airtrap}$ or $DPM_{emph}$) may be calculated and displayed individually for a set of images single point in time, or side by side for a longitudinal assessment of two or more points in time. The side by side comparison in FIGS. 14A and B show a decrease in the amount of normal tissue from the first time point to the second time point.

The side by side comparisons of lung representation in these examples are shown for the same lung cross section in each representation. In order to provide the images in this way, the representations at each time point must be registered to each other. Some embodiments of the invention therefore include the step of registering a first set of lung images at a first time to a second set of images at a second point in time. Additional image sets may also be registered together at additional points in time. For example, in some embodiments, the registration may include achieving a voxel by voxel alignment of the images at the first time point to the set of images at the second time point. In one embodiment, a first set of images at a first time point is used as a reference domain. This set of images may be the inspiratory or the expiratory set. A second set of images at a second time point is then registered to the reference domain, using the same type of image set (e.g. inspiratory or expiratory) as in the reference domain. This registration of the images at a first and second time point may be used to allow the side by side comparison of the lung representations as described. It may further be used to calculate differences between the images at the first and second time point, which may be presented visually as described further below.

Figure 16:
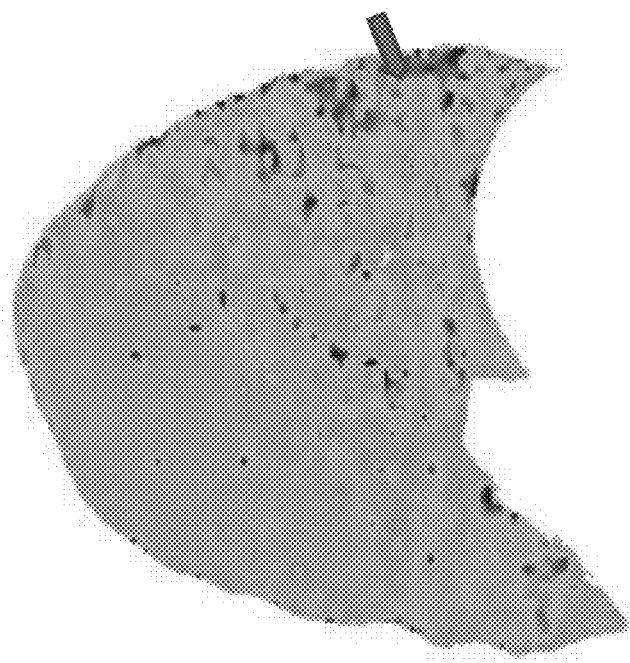
FIG. 16 is a 3 dimension lung representation showing the change between the $DPM_{Normal}$ values for each voxel in FIG. 14A as compared to FIG. 14B.
Figure 17:
FIG. 17 is a key to the color scale used in FIG. 16.

In some embodiments, a visual representation may be created with is a difference map, such as showing the difference between the lung characteristic, disease probability measure, or classification into states, between the first time point and the second time point. Such a visual representation facilitates the visualization of areas with parenchymal change as well as the understanding of the magnitude of the changes, on a continuous scale. A color scale may be used to represent the difference, which may be used to reveal both improvements and worsening of a characteristic, disease probability, or state. An example of such a difference map is shown in FIG. 16, which represents the difference between the $DPM_{Normal}$ values of FIGS. 14A and 14B, on a voxel by voxel basis. A key to the color spectrum used in FIG. 16 is shown in FIG. 17. As shown in FIG. 17, a difference of −1 is represented by red and indicates a large improvement, the presence of no change (a value of zero) is represented by green, and a difference of 1 is represented by blue and indicates a large degree of worsening. It can be seen that some portions of the lung remained unchanged relatively, while other portions worsened. In particular, an area of worsened condition can be easily seen and is marked by the red arrow. This visual representation allows the clinician to see where change is occurring in the lungs as well as the magnitude of the change.

Figure 18:
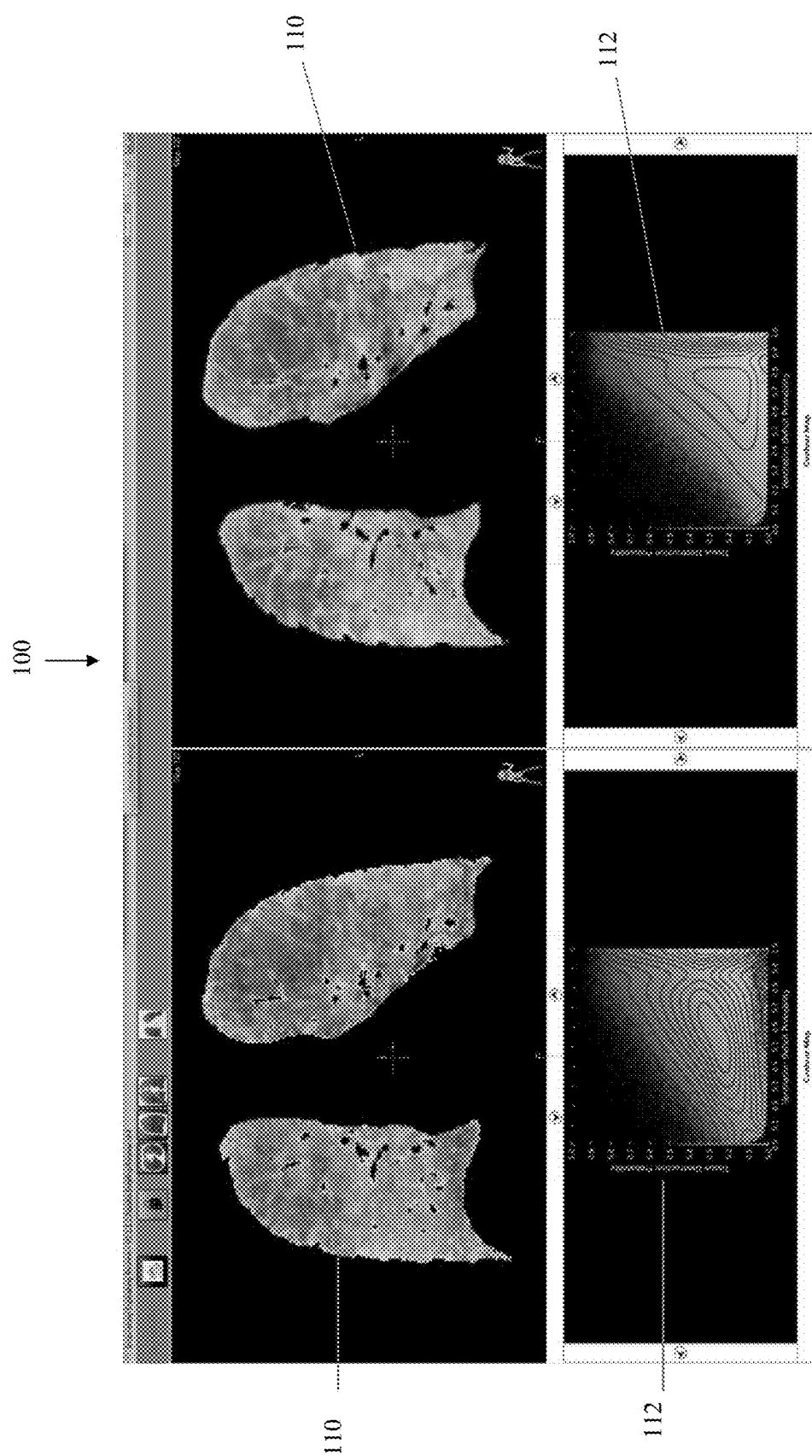
FIG. 18 is an example of a graphical user interface including 3 dimensional lung representations and lung prints at first and second time points for longitudinal assessment.

An example of a graphical user interface 100 which may be used for longitudinal assessment of lung function is shown in FIG. 18. On the left half of the screen, a 3 dimensional lung representation 110 from lung images obtained at a first time is shown in which a continuous spectrum of colors correlates to the probability of tissue destruction and ventilation deficit at every paired voxel location. The corresponding lung print 112 for the first time is also shown. On the right half of the screen, a 3 dimensional lung representation 110 from lung images obtained at a second later time is shown. Again, the continuous spectrum of colors correlates to the probability of tissue destruction and ventilation deficit at every paired voxel location.

The corresponding lung print 112 for the second time is also shown. In this example, the first time is a baseline and the second time is at a follow-up appointment. The side-by-side representations allow a user to more easily see the differences in the patient's lungs over time.

In addition to the voxel-by-voxel comparison of the two time points described above, more sophisticated transformations may be made and displayed for a clinician. For example, image segmentation and classification techniques could be applied on to the continuous scale of characteristics or of probabilities to identify and highlight areas with a given range of change in characteristics or DPM probability values. Such comparisons may likewise be displayed as images which are three dimensional lung representations with color spectrums corresponding to the amount of change.

The analysis as described herein may be used for diagnosing and monitoring COPD and may also be used for assessing the risk for lung cancer and for providing guidance regarding lung cancer screening. For example, particular patterns of lung characteristics or lung function, lung prints, lung disease probability, or lung state classification may be associated with increased or decreased risk of lung cancer. Lung cancer screening recommendations may therefore take a patient's functional analysis as described herein into account when recommending a lung cancer screening schedule (such as increasing or decreasing the frequency of screening as compared to a baseline recommendation based only on demographics).

Figure 19:
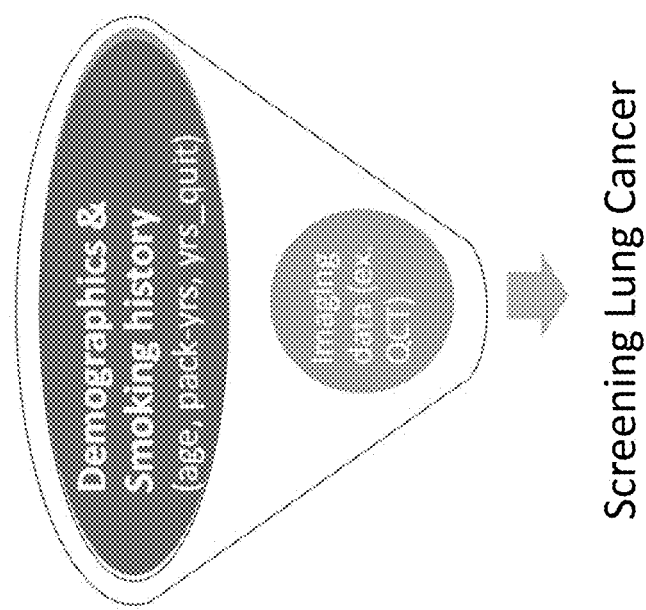
FIG. 19 shows a representation of how embodiments may be used to refine cancer screening recommendations.

For example, as shown in FIG. 19 a broad based approach may be used for lung cancer screening recommendations, based upon patient demographics and smoking history, such as age, pack years of smoking, and years since smoking cessation. However, cancer risk and response to smoking varies among individuals, and this variability is reflected in functional lung changes which can be detected using the imaging data as described herein to reduce the number of patients for which screening (such as annual lung CT) is recommended, providing a significant cost savings. Various embodiments may therefore use the calculations described herein to determine a more refined lung cancer screening protocol and may display this recommended protocol for the clinician.

Example 1

Figure 20:
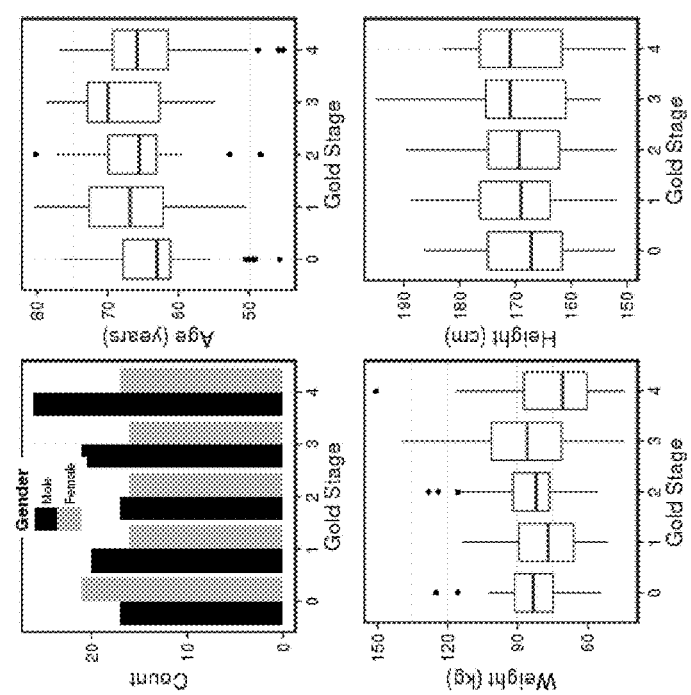
FIG. 20 shows the demographics of the patients whose data was used in the examples.

Various examples were performed to compare the diagnostic capabilities of the registration methods described herein with other methods. A group of 188 subjects previously diagnosed with COPD at various GOLD stages were used for these examples. The gender, age, weight, and height of the patients in each GOLD stage are shown in FIG. 20. For each subject, full inspiration and full expiration CT images were registered and DPM values were calculated as described above.

Figure 21:
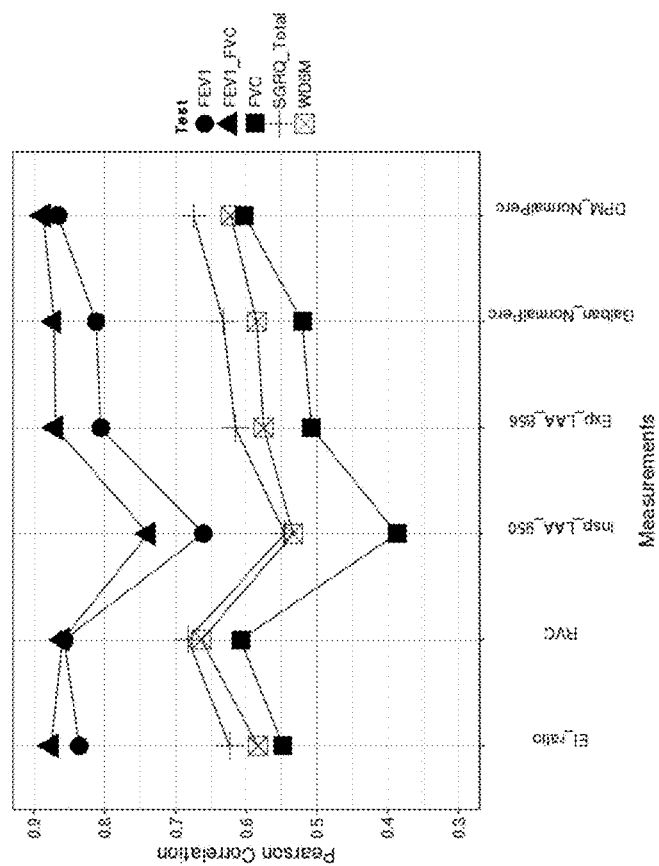
FIG. 21 shows the statistical correlation between various CT methods of measuring lung disease and various clinical methods.

CT based lung function measurements were calculated using the CT images of the subjects, including the EI ratio, the relative volume change between −860 HU and −950 HU (referred to as RVC), gas trapping measurements (referred to as Exp_LAA_856), and percentage of normal tissue computed using a threshold-based registration method (referred to as Galban NormalPerc). Each of these values, as well as the DPM derived normal tissue percentage (DPM_NormalPerc) value, was compared to clinical measurements of lung function including FEV1, FEV_FVC, FVC, St. George's Respiratory Questionnaire total score (referred to as SGRQ_Total), and 6 minute walking distance (referred to as WD6M), to determine the statistical correlation. The results are shown in the graph in FIG. 21, in which the Pearson Correlation is shown for each comparison. It can be seen that the DPM_NormalPerc measurement had a correlation to clinical measurements that was equal to or better than any other CT based calculations. In particular, there is a strong correlation between DPM_NormalPerc and FEV1. This reinforces the value of DPM-based measurements to quantify air flow limitations.

The statistical comparison between the value of Galban NormalPerc (which is based on cut-off values) and the clinical measurement, and between DPM_NormalPerc (which is based on continuous measurements) and the clinical measurements, is shown in Table 1 with the Pearson Correlation (r) and regression p-value. In all cases, the DPM_NormalPerc shows a stronger correlation with the clinical measurements and higher predictability than the Galban NormalPerc method.

ment for small airway disease than other spirometric values. Exacerbation frequency and chronic bronchitis are also believed to relate to small airway disease. Because of this, the DPM_AirTrapPerc and DPM_EmphPerc were compared to FEF25-75%, COPD exacerbation frequency, and chronic bronchitis. The exacerbation frequency was ranked as zero if the patient had no exacerbation and as greater than or equal to one if one or more exacerbations occurred within prior year. Bronchitis was ranked as zero (absent) or one (present) depending upon clinical diagnosis by a physician.

Figure 23:
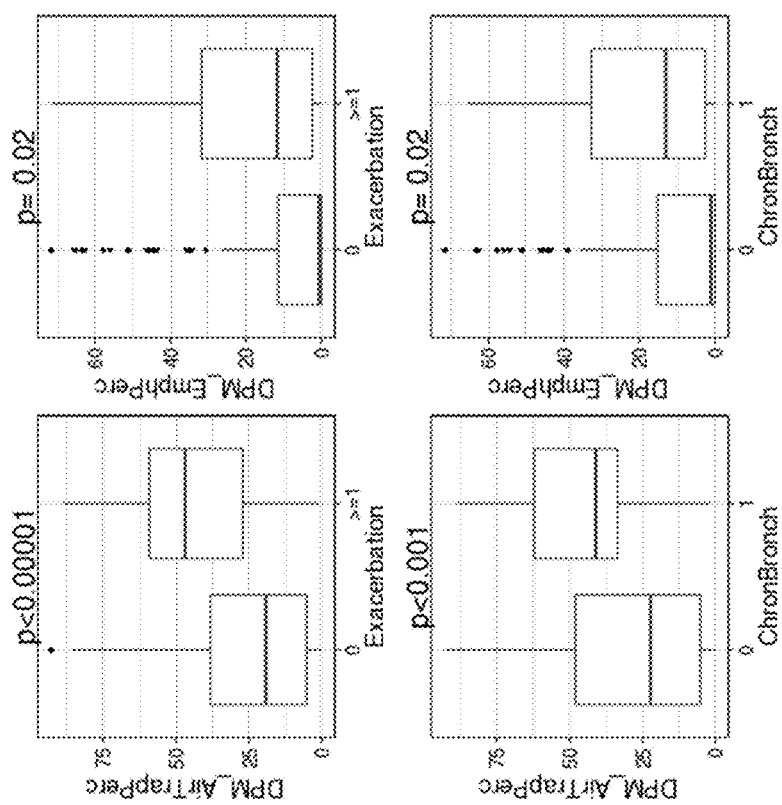
FIG. 23 shows a box lot of DPM_AirTrapPerc and DPM_EmphPerc to COPD exacerbation and chronic bronchitis.

When DPM_AirTrapPerc was compared to FEF25-75%, the Pearson correlation coefficient was −0.63. When DPM_EmphPerc was compared to FEF25-75%, the Pearson correlation coefficient was −0.47. The correlation between each of DPM_AirTrapPerc or DPM_EmphPerc and exacerbation or chronic bronchitis is shown in the boxplots of FIG. 23, in which the p-value for each is also shown. These show a strong association between DPM_AirTrapPerc and the

TABLE 1

|  | Pearson Correlation (r) | | Regression (p-value) | |
| --- | --- | --- | --- | --- |
|  | Galban_NormalPerc | DPM_NormalPerc | Galban_NormalPerc | DPM_NormalPerc |
| FEV1 | 0.81 | 0.87 | 0.97 | $6.6\ 10^{-14}$ |
| FVC | 0.52 | 0.60 | 0.036 | $8.7\ 10^{-8}$ |
| FEV1/FVC | 0.87 | 0.89 | $6.3\ 10^{-4}$ | $7.0\ 10^{-9}$ |
| FEF 25-75% | 0.63 | 0.69 | 0.46 | $4.8\ 10^{-9}$ |
| 6MWD | 0.59 | 0.62 | 0.88 | $4.2\ 10^{-4}$ |
| SGRQ | −0.63 | −0.67 | 0.98 | $3.3\ 10^{-5}$ |

Figure 22:
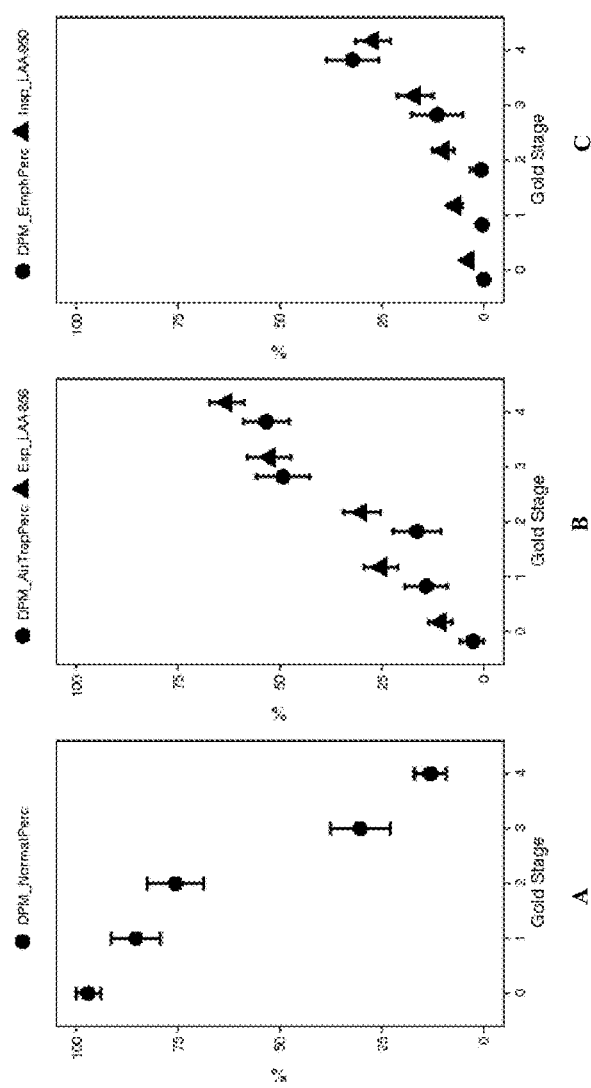
FIG. 22A charts mean DPM_NormalPerc by GOLD Stage.
FIG. 22B charts DPM_AirTrapPerc and Exp-LAA-856 by GOLD Stage.
FIG. 22C charts DPM_EmphPerc and Insp-LAA-950 by GOLD Stage.

In FIG. 22A-C, the mean DPM measurements and 95% confidence intervals are shown by GOLD stage. In the graph shown in FIG. 22A, the DPM_NormalPerc is shown for each GOLD Stage and falls from nearly 100% for GOLD Stage 0 to about 12% for GOLD Stage 4, indicating a strong correlation with GOLD State. In the graph shown in FIG. 22B, the DPM_AirTrapPerc values rise steadily from nearly zero at GOLD Stage 0 to about 55% for GOLD Stage 4. The mean values and 95% confidence intervals for Exp_LAA-856 are also shown. In the graph shown in FIG. 22C, DPM_EmphPerc values are shown by GOLD stage, along with the mean values and 95% confidence interval for Insp_LAA-950. The DPM_EmphPerc rises from around zero for GOLD Stage 0 to around 30% for GOLD Stage 4. In all cases, a good correlation can be seen between the DPM measurements, GOLD stage, and the traditional quantitative CT measurements.

The DPM_NormalPerc values were further analyzed within each GOLD Stage and compared to the DPM_NormalPerc values for each of the other GOLD Stages to determine if there is a statistical difference. The resulting p-values are shown in Table 2, below. As can be seen, there was a statistically significant difference for all of the comparisons except between GOLD 1 and GOLD 2.

TABLE 2

| GOLD | 0 | 1 | 2 | 3 |
| --- | --- | --- | --- | --- |
| 1 | <0.01 | — | — | — |
| 2 | <0.00001 | 0.59 | — | — |
| 3 | <0.00001 | <0.00001 | <0.00001 | — |
| 4 | <0.00001 | <0.00001 | <0.00001 | <0.001 |

Currently there is no direct physical measurement of the amount of emphysema or air-trapping in tissue itself. However, FEF25-75% is believed to be a more specific measure-presence of COPD exacerbation and chronic bronchitis, indicating that DPM_AirTrapPerc is a good measure of small airway disease.

In additional analysis, it was found that DMP_AirTrapPerc is weakly correlated with traditional emphysema metrics such as Insp_LAA_950, with a Pearson correlation coefficient of 0.31. In contrast, the correlation between measurements of small airway disease using cut-off values as taught by Galban et. al and Insp_LAA_950 had a Pearson correlation coefficient of 0.69 which may indicate that the cut-off method of calculation not only captures airway disease but probably some emphysema as well.

Example 2

In another example, the CT images of current and former smokers were analyzed to determine whether the functional assessments described herein could be used to refine existing lung cancer screening guidelines through the use of independent quantitative CT (QCT) biomarkers of lung cancer.

Full inspiration and expiration CT images were obtained from 322 current or former smokers between the ages of 40 and 89 years old. Of these subjects, 42.5% (n=137) had proven lung cancer, and cancer staging was available for 101 subjects, which included 27.7% stage I (IA=17; IB=11), 18.8% stage II (IIA=11; IIB=8), 27.7% stage III (IIIA=18; IIIB=10), and 25.7% stage IV (IV=26). The images of each patient were processed and registered using nonlinear lung registration, CT functional measurements were calculated, and disease probability measurements were determined as described herein, including DPM_AirTrapPerc, DPM_EmphPerc, and DPM_NormalPerc.

A logistic regression analysis was performed for the presence of lung cancer to determine the predictive power of CT registration-based DPM measurements (DPM_NormalPerc, DPM_AirTrapPerc, DPM_EmphPerc) for the presence of lung cancer. Confounding variables/factors recommended by the American Cancer Society as indicating the need for lung cancer screening including age, number of pack-years of smoking (referred to as Pack-year), and years since smoking cessation (referred to as Years_quit) were included in the regression model as well as all regression-based measurements. In this preliminary analysis, no other imaging variable was considered.

The main predictors of lung cancer from the final regression model were: Years_quit ($p<0.0001$), DPM_AirTrapPerc ($p=0.006$), Pack_years ($p=0.008$), Age ($p=0.017$), BMI ($p=0.064$), and their interaction of Pack-year*Age (the combination of pack-year and age)($p=0.092$). Of all the variables, Pack-year satisfied the assumption of linearity in the logit and was kept continuous. All other variables were categorized. The odds ratio for lung cancer increased by about 2.49× (CI=[1.30,4.76]) when DPM_AirTrapPerc was greater than or equal to 15% as compared to when DPM_AirTrapPerc was less than 15%. This indicates that the presence or absence of DPM_AirTrapPerc may be considered when recommending lung cancer screening.

These results show that CT functional air trapping measurement is a significant predictor of lung cancer and can be used to incrementally refine existing screening guidelines based on demographics and smoking history. Other QCT measurements of lung structure and lung function characterizing airway remodeling, airway obstruction, lung compliance, and evolution of lung health status are also likely to improve the existing patient selection screening model.

In the foregoing detailed description, the invention has been described with reference to specific embodiments. However, it may be appreciated that various modifications and changes can be made without departing from the scope of the invention.

The invention claimed is:

1. A method of assessing lung function using a first set of lung volumetric images obtained at inspiration and a second set of volumetric images obtained at expiration, the method comprising:
   a) processing the first and second set of images to identify known anatomical structures of the lungs;
   b) registering the first set of images to the second set of images to match voxels of the first set of images to voxels of the second set of images as matched pairs of inspiratory and expiratory voxels;
   c) calculating a probability of a lung characteristic at each of a plurality of locations, each of the plurality of locations corresponding to one of the matched pairs of voxels of step b); and
   d) displaying a result of step c) on a display, the displayed result comprising the calculated probability or a different value derived from the calculated probability at each of a plurality of locations of matched pairs of voxels.

2. The method of claim 1 wherein displaying the result comprises generating an image depicting a set of data points, wherein each data point represents the calculated probability of the lung characteristics at the plurality of locations of the matched pairs of voxels of step c).

3. The method of claim 2 wherein the image comprises a 3 dimensional representation of the lungs and/or a 2 dimensional representation of the lungs, wherein each data point is depicted in the representation at a location corresponding to the location of the matched pair of voxels.

4. The method of claim 1 further comprising:
   e) registering a third set of images obtained at inspiration to a fourth set of images obtained at expiration as matched pairs of inspiratory and expiratory voxels,
   f) calculating the probability of the lung characteristic at locations of the matched pairs of voxels of step e); and
   g) displaying a result of step f) on the display,
   wherein the first and second sets of images were obtained at a first time, and the third and fourth sets of images were obtained at a second later time.

5. The method of claim 1 wherein the probability of a lung characteristic is a combination of a probability of tissue destruction and a probability of a ventilation deficit.

6. The method of claim 5 wherein displaying the result comprises generating a color image depicting a set of data points, wherein the color of each data point represents the calculated probability of the lung characteristic of the matched pairs of voxels of step c), and wherein the color of each data point is a composite of a first color component dependent upon the probability of a ventilation deficit and a second color component dependent upon the probability of tissue destruction.

7. The method of claim 6 wherein each data point is displayed on a graph with the probability of tissue destruction on a first scale and probability of ventilation deficit on a second scale.

8. The method of claim 7 wherein the graph further comprises a plurality of topographic lines, wherein each topographic line indicates an equal number of data points occurring at all coordinates on each topographic line.

9. The method of claim 6 wherein the color image comprises a 3 dimensional representation of the lungs and/or a 2 dimensional representation of the lungs, wherein each data point in the representation is located at a location corresponding to a location of the matched pair of voxels in the patient's lungs.

10. The method of claim 1 further comprising classifying lung tissue at the locations of the matched pairs of voxels step c) by using the calculated probability as being normal or being abnormal.

11. The method of claim 10 further comprising classifying the lung tissue which is abnormal as having air trapping only without emphysema, or as having emphysema.

12. A system for assessing and displaying lung function using a first set of lung volumetric images obtained at inspiration and a second set of volumetric images obtained at expiration from a patient, the system comprising:
   a display;
   a processor;
   computer readable medium;
   software executable by the processor, the software configured to:
      a) process the first and second set of images to identify known anatomical structures of the lungs;
      b) register the first set of images to the second set of images to match voxels of the first set of images to voxels of the second set of images as matched pairs of inspiratory and expiratory voxels;
      c) calculate a probability of a lung characteristic at each of a plurality of locations, each of the plurality of locations corresponding to one of the matched pairs of voxels of step
      d) generate an image depicting a set of data points, wherein each data point represents the calculated probability of each of the matched pairs of voxels of step c) or a different value derived from the probability of the lung characteristic of each of the matched pairs of voxels of step c); and e) present the image to a user on the display.

13. The system of claim 12 wherein each data point is depicted in the representation at a location corresponding to a location of the matched pair of voxels in the patient's lungs.

14. The method of claim 13 wherein the probability of a lung characteristic is a probability of tissue destruction and a probability of a ventilation deficit.

15. The method of claim 14 wherein the image comprises a plurality of colors in a color spectrum, and wherein the color of each data point is a composite of a first color component dependent upon the probability of a ventilation deficit and a second color component dependent upon the probability of tissue destruction.

16. The system of claim 12, the software further configured to calculate a probability of a tissue being normal at the location in the lung corresponding to each matched pair of voxels of step c) using the probability of the lung characteristic.

17. The system of claim 16, the software further configured to calculate a probability of the tissue being emphysematous and a probability of the tissue having air trapping without emphysema at the location in the lung corresponding to each matched pair of voxels of step c) using the probability of the lung characteristic.

18. The system of claim 17, the software further configured to use the probabilities of the tissue being normal, emphysematous, or having air trapping without emphysema to classify the tissue as normal, emphysematous, or having air trapping without emphysema at the location in the lung corresponding to each matched pair of voxels of step c).

19. The system of claim 18 wherein the image comprises a visual representation of the lungs using colors corresponding to the classification at the location of each matched pair of voxels, wherein the visual representation comprises a 3 dimensional representation of the lungs and/or a 2 dimensional representation of the lungs.

20. A system for assessing pulmonary function via a visual representation of a lung of a patient, the system comprising:

a processor;

a graphical user interface; and a non-transitory computer-readable medium comprising executable instructions for causing the processor to generate the visual representation and present the visual representation on the graphical user interface; wherein the visual representation is colored to represent a probability of a lung characteristic at each location in the image, the probability is calculated for each location in matched pairs of voxels in patient CT images at inspiration and expiration, and the visual representation comprises a 3 dimensional representation of a lung and/or a 2 dimensional representation of a lung.

* * * * *